United States Patent
Sabat et al.

(10) Patent No.: US 7,256,196 B1
(45) Date of Patent: Aug. 14, 2007

(54) PURINE CYTOKINE INHIBITORS

(75) Inventors: Mark Sabat, Mason, OH (US); Michael Philip Clark, Maineville, OH (US); Todd Andrew Brugel, West Chester, OH (US); Adam Golebiowski, Loveland, OH (US); John Charles Van Rens, Cincinnati, OH (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 435 days.

(21) Appl. No.: 11/006,095

(22) Filed: Dec. 7, 2004

Related U.S. Application Data

(60) Provisional application No. 60/527,966, filed on Dec. 9, 2003.

(51) Int. Cl.
*C07D 473/16* (2006.01)
*C07D 473/18* (2006.01)
*C07D 473/28* (2006.01)
*A61K 31/522* (2006.01)
*A61K 31/52* (2006.01)

(52) U.S. Cl. .............. 514/263.23; 544/264; 544/265; 544/276; 544/277; 544/118; 544/247; 514/263.3; 514/263.37; 514/263.38; 514/263.4

(58) Field of Classification Search ............... 544/264, 544/265, 276, 277, 118, 247; 514/257, 234.2, 514/263.4, 263.38, 263.37, 263.3, 263.23
See application file for complete search history.

(56) References Cited

U.S. PATENT DOCUMENTS

| 3,133,065 A | 5/1964 | Carbon | |
| 6,579,868 B1 * | 6/2003 | Asano et al. | 514/211.08 |
| 2006/0287344 A1 * | 12/2006 | Albers et al. | 514/263.2 |
| 2007/0060598 A1 * | 3/2007 | Albers et al. | 514/263.23 |

FOREIGN PATENT DOCUMENTS

WO  WO 2005/016528 A2  2/2005

OTHER PUBLICATIONS

Thompson, R.D. et al., "$N^6$,9-Disubstituted Adenines: Potent, Selective Antagonists at the $A_1$ Adenosine Receptor", *J. Med. Chem.*, 1991, pp. 2877-2882, vol. 34.

Nagano, H. et al., "Fluorine-Containing Potential Anticancer Agents. II. Syntheses of Some Trifluoromethylpurines and Trifluoromethylthiazolopyrimidines", *J Med Chem.*, 1964, pp. 215-220, vol. 7, No. 2.

Koppel, H. et al., "Potential Purine Antagonists. XI Synthesis of Some 9-Aryl(alkyl)-2, 6-disubstituted Purines", *J. Amer. Chem. Soc.*, 1958, pp. 2751-2755, vol. 80.

* cited by examiner

*Primary Examiner*—Mark L. Berch
(74) *Attorney, Agent, or Firm*—Andrew A. Paul

(57) ABSTRACT

The present invention relates to 2,8,9-substituted purines which inhibit the extracellular release of inflammatory cytokines, said cytokines responsible for one or more human or higher mammalian disease states. The present invention further relates to compositions comprising said 2,8,9-substituted purines and methods for preventing, abating, or otherwise controlling enzymes which are understood to be the active components responsible for the herein described disease states.

6 Claims, No Drawings

PURINE CYTOKINE INHIBITORS

CROSS REFERENCE TO RELATED APPLICATIONS

This application claims priority under Title 35, United States Code 119(e) from Provisional Application Ser. No. 60/527,966, filed Dec. 9, 2003.

FIELD OF THE INVENTION

The present invention relates to 2,8,9-substituted purines which inhibit the extracellular release of inflammatory cytokines, compositions comprising said 2,8,9-substituted purines, and methods for preventing, abating, or otherwise controlling the extracellular release of inflammatory cytokines.

DETAILED DESCRIPTION OF THE INVENTION

It has been surprisingly found that certain 2-heterocycloamino-8-[substituted or unsubstituted]acyl-9-alkyl purines and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The present invention relates to purines, for example, 2-heterocycloamino-8-[substituted or unsubstituted]acyl-9-alkyl purines are suitable for mediating, controlling or otherwise inhibiting the extracellular release of certain cytokines, especially inflammatory cytokines, said cytokines playing a role in the stimulation, cause or manifestation of a wide variety of diseases, disease states, or syndromes.

The following chemical hierarchy is used throughout the specification to particularly point out and distinctly claim the units which comprise the compounds of the present invention. The term "hydrocarbyl" stands for any organic molecule, organic functional group, including inorganic atom comprising salts, inter alia, carboxylate salts, quaternary ammonium salts, or for any portion, unit, moiety, and the like, of an organic molecule. Encompassed within the term "hydrocarbyl" are the terms "acyclic" and "cyclic" units which divide hydrocarbyl into cyclic and non-cyclic classes. Acyclic units include alkyl, alkenyl, alkynyl units and their corresponding connecting units, inter alia, alkylene, all of which can be substituted by the suitable substitutions for hydrogen defined herein. Encompassed within the term "cyclic hydrocarbyl" are the carbocyclic, heterocyclic, aryl, and heteroaryl units, and their corresponding connecting units, inter alia, arylene, all of which can be substituted by the suitable substitutions for hydrogen defined herein. Included within the carbocyclic definition are spirocyclic rings, bicyclic rings, and bridged bicyclic rings, as well as fused rings, inter alia, tetralin. For the purposed of the present invention fused ring units which comprise a single heteroatom within a non-aromatic ring, for example, 1,2,3,4-tetrahydroquinoline having the formula:

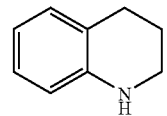

is considered a heterocyclic ring, while 6,7-dihydro-5H-[1]pyridine having the formula:

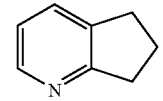

is considered a heteroaryl unit since the heteroatom comprises an aromatic ring.

Included within the definition of "hydrocarbyl" as defined herein above, are the aromatic (aryl) and non-aromatic (carbocyclic) rings, non-limiting examples of which include cyclopropyl, cyclobutanyl, cyclopentanyl, cyclohexanyl, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

Included within the definition of "hydrocarbyl" as defined herein above, are the heteroatom-comprising aromatic (heteroaryl) and non-aromatic (heterocyclic) rings, non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

The term "aryloyl" as it relates to units attached to the core pyrrolo[2,3-d]pyrimidine scaffold further defined herein below. A non limiting example of an aryloyl substituent is a substituted or unsubstituted benzoyl unit having the general formula:

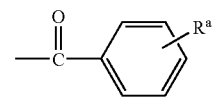

wherein $R^a$ represents one or more possible substitutions for a hydrogen atom.

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit", 3-guanidinopropyl is a "substituted $C_3$ alkyl unit," and 2-carboxypyridinyl is a "substituted heteroaryl unit."

The following are non-limiting examples of units which can substitute for hydrogen atoms on a hydrocarbyl or other unit:
i) —$OR^{12}$;
ii) —$C(O)R^{12}$;
iii) —$C(O)OR^{12}$
iv) —$C(O)N(R^{12})_2$;
v) —CN;
vi) —$N(R^{12})_2$;
vii) —halogen; and
viii) —$CF_3$, —$CCl_3$, —$CBr_3$;

wherein $R^{12}$ is hydrogen, substituted or unsubstituted $C_1$-$C_4$ linear, branched, or cyclic alkyl, and mixtures thereof.

The compounds of the present invention are purines having the core scaffold:

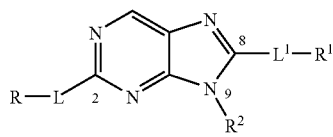

wherein the numbered positions on the ring relate to the naming and substitutions at each position described herein.

R units which comprise the compounds of the present invention are chosen from:
i) substituted or unsubstituted $C_6$-$C_{10}$ aryl;
ii) substituted or unsubstituted $C_1$-$C_6$ linear or branched acyclic hydrocarbyl;
iii) substituted or unsubstituted $C_1$-$C_{10}$ heterocyclic; and
iv) substituted or unsubstituted $C_1$-$C_{10}$ heteroaryl.

The first aspect of R units relates to substituted or unsubstituted $C_6$-$C_{10}$ aryl units, that is aryl units comprising from 6 to 10 carbon atoms, wherein said substitution is chosen from: halogen, $C_1$-$C_4$ linear or branched alkyl, —OH, —$OR^7$, —CN, —$N(R^7)_2$, —$CO_2R^7$, —$CON(R^7)_2$, —$NR^7COR^7$, and —$NO_2$; each $R^7$ is independently hydrogen, $C_1$-$C_4$ alkyl, or two $R^7$ units can be taken together to form a ring comprising from 3-7 atoms.

The first iteration of this aspect encompasses units chosen from: phenyl, 2-fluorophenyl, 3-fluorophenyl, 4-fluorophenyl, 2,4-difluorophenyl, 3,5-difluorophenyl, 2,6-difluorophenyl, 2-chlorophenyl, 3-chlorophenyl, 4-chlorophenyl, 2,4-dichlorophenyl, 3,5-dichlorophenyl, and 2,6-dichlorophenyl.

A second iteration of this aspect relates to aryl units substituted with a unit chosen from:
i) —$CO_2R^7$;
ii) —$CON(R^7)_2$; and
iii) —$NR^7COR^7$;

wherein $R^7$ is hydrogen, methyl, or ethyl

The third iteration of this aspect relates to aryl units chosen from 2-methylphenyl, 3-methylphenyl, 4-methylphenyl, 2,4-dimethylphenyl, 3,5-dimethylphenyl, 2,6-dimethylphenyl, 2-methoxyphenyl, 3-methoxyphenyl, 4-methoxy-phenyl, 2,4-dimethoxyphenyl, 3,5-dimethoxyphenyl, and 2,6-dimethoxyphenyl.

The second aspect of R units relates to substituted or unsubstituted 5-member ring $C_1$-$C_4$ heterocyclic units, that is heterocyclic units comprising from 1 to 4 carbon atoms. The first iteration of this aspect encompasses units chosen from pyrrolidin-1-yl, pyrrolidin-4-yl, tetrahydrofuran-2-yl, imidazolidin-2-yl, imidazolidin-4-yl, isoxazol-3-yl, and 5-methylisoxazol-3-yl.

The third aspect of R units relates to substituted or unsubstituted 6-member ring $C_1$-$C_5$ heterocyclic units, that is heterocyclic units comprising from 1 to 5 carbon atoms. The first iteration of this aspect encompasses units chosen from piperidin-1-yl, piperidin-4-yl, morpholin-4-yl, and pyran-4-yl.

The fourth aspect of R units relates to substituted or unsubstituted $C_1$-$C_6$ linear or branched alkyl unit having the formula:

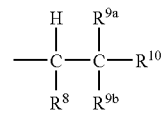

wherein $R^8$, $R^{9a}$, $R^{9b}$, and $R^{10}$ are each independently;
i) hydrogen;
ii) $C_1$-$C_4$ alkyl;
iii) —OH; or
iv) $C_1$-$C_4$ alkoxy.

A first iteration of this aspect includes chiral R units, for example, units having the formula:

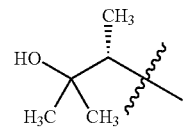

Non-limiting examples of other R units which are encompassed by this iteration include units chosen from 2-methyl-2-hydroxy-1-(S)-methylpropyl, 2-methoxy-1-(S)-methylethyl, 2-methyl-2-cyano-1-(S)-methylpropyl, 2-methyl-2-hydroxy-1-(R)-methylpropyl, 2-methoxy-1-(R)-methylethyl, 2-methyl-2-cyano-1-(R)-methylpropyl, 1-(S)-methylpropyl, and 1-(R)-methylpropyl.

Another iteration includes the racemic mixtures of substituted and unsubstituted $C_1$-$C_6$ alkyl units, for example, units chosen from 1,2-dimethyl-2-hydroxypropyl, 2-methoxy-1-methylethyl, 1,2-dimethyl-2-cyanopropyl, and 1-methylpropyl.

$R^1$ is chosen from:
  i) hydrogen; and
  ii) substituted or unsubstituted $C_6$-$C_{10}$ aryl.

The first aspect of $R^1$ relates to aryl units chosen from phenyl, 2-fluorophenyl, 3-fluorophenyl, 4-fluorophenyl, 2,4-difluorophenyl, 3,5-difluorophenyl, 2,6-difluorophenyl, 2-chlorophenyl, 3-chlorophenyl, 4-chlorophenyl, 2,3-dichlorophenyl, 2,4-dichlorophenyl, 3,5-dichlorophenyl, 2,6-dichlorophenyl, 2-fluoro-5-chlorophenyl, 2-chloro-5-fluorophenyl, 2-chloro-5-methylphenyl, and 2-chloro-5-trifluoromethylphenyl.

The second aspect of $R^1$ relates to aryl units chosen from 2-aminophenyl, 3-aminophenyl, 4-aminophenyl, 2-nitrophenyl, 3-nitrophenyl, 4-nitrophenyl, 2-methoxy-phenyl, 3-methoxyphenyl, 4-methoxyphenyl, 2-hydroxyphenyl, 3-hydroxyphenyl, 4-hydroxyphenyl, 3-methylcarboxyphenyl.

$R^2$ is chosen from:
  i) $C_1$-$C_6$ linear, branched or cyclic alkyl;
  ii) substituted or unsubstituted $C_6$-$C_{10}$ aryl; and
  iii) $-[C(R^6)_2]_xCO_2R^6$.

The first aspect of $R^2$ relates to aryl units chosen from hydrogen, methyl, ethyl, propyl, isopropyl, cyclopropyl, and cyclopropylmethyl. A first iteration of this aspect relates to compounds wherein $R^2$ is methyl. A second iteration of this aspect relates to compounds wherein $R^2$ is ethyl. A third iteration of this aspect relates to compounds wherein $R^2$ is isopropyl.

The second aspect of $R^2$ relates to aryl units chosen from 2-hydroxy-2-methyl-1-(S)-methylpropyl, 2-hydroxyethyl, $-CH_2CO_2H$, and $-CH_2CO_2CH_3$.

L and $L^1$ are linking units each of which independently has the formula:

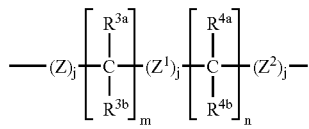

Z, $Z^1$, and $Z^2$ are each independently a unit chosen from:
  i) $-NR^5-$;
  ii) $-O-$;
  iii) $-C(O)-$;
  iv) $-CHOR^5-$;
  V) $-SO_2-$;
  vi) $-NR^5 SO_2-$; and
  vii) $-SO_2NR^5-$;

each of the indices j is independently 0 or 1. Each $R^5$ unit is independently chosen from:
  i) hydrogen;
  ii) substituted or unsubstituted $C_1$-$C_4$ linear, branched, or cyclic alkyl;
  iii) $-COR^6$;
  iv) $-[C(R^6)_2]_xCO_2R^6$; or
  v) $-[C(R^6)_2]_xCON(R^6)_2$;

$R^6$ is hydrogen, $C_1$-$C_4$ substituted or unsubstituted alkyl, or two $R^6$ units on adjacent carbon atoms can be taken to form a double bond;

$R^{3a}$, $R^{3b}$, $R^{4a}$, and $R^{4b}$ are each independently:
  i) hydrogen;
  ii) $-OR^6$;
  iii) halogen;
  iv) $-[C(R^6)_2]_xCO_2R^6$; or
  v) $-[C(R^6)_2]_xCON(R^6)_2$;
  vi) $C_1$-$C_4$ linear, branched, or cyclic alkyl,
  vii) halogen substituted $C_1$-$C_4$ linear, branched, or cyclic alkyl,
  viii) $C_1$-$C_4$ linear, branched, or cyclic alkoxy,
  ix) $R^{3a}$ and $R^{3b}$ or $R^{4a}$ and $R^{4b}$ can be taken together to form a unit having the formula: C=X wherein X is O, S, $NR^5$, or $NOR^7$; $R^7$ is hydrogen, $C_1$-$C_4$ linear alkyl, and $-COR^6$;
  x) two $R^{3b}$ or two $R^{4b}$ units from adjacent carbon atoms can be taken together to form a double bond;
  xi) $R^{3a}$ and $R^{3b}$ or $R^{4a}$ and $R^{4b}$ can be taken together to form a ring comprising from 3 to 7 atoms; and
  xii) $R^{3a}$ and $R^{3b}$ or $R^{4a}$ and $R^{4b}$ can be taken together to form a unit chosen from $=CH[C(R^6)_2]_xCO_2R^6$, $=CH[C(R^6)_2]_xCON(R^6)_2$, and $=CH[C(R^6)_2]_xOC(O)R^6$;

the indices m and n are each independently from 0 to 5; x is from 0 to 5.

The first aspect of linking groups relates to compounds wherein L and $L^1$ are each independently chosen from:
  i) $-NH-$;
  ii) $-O-$;
  iii) $-SO_2-$;
  iv) $-C(O)-$;
  v) $-C=NOR^6$;
  vi) $-C(R^6)_2-$;
  vii) $-C[=C(R^6)_2]-$; and
  viii) $-C(OR^5)_2-$;

wherein $R^5$ is hydrogen, $-COR^6$, or two $R^5$ units can be taken together with the oxygen atoms to form a cyclic ketal ring comprising 5 or 6 atoms; $R^6$ is methyl, ethyl, or n-propyl.

A second aspect relates to $L^1$ units which have the formula $-NR^5-$ and $R^5$ is a unit chosen from:
  i) $-CH_2CO_2H$;
  ii) $-CH_2CO_2CH_3$;
  iii) $-CH_2CO_2C(CH_3)_3$;
  iv) $-CH_2CH_2OH$;
  v) $-CH_2CONHCH_3$; and
  vi) $-CH_2CON(CH_3)_2$.

A third aspect of linking group relates to compounds having the formula:

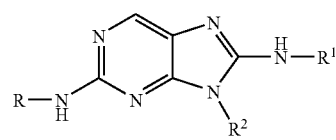

wherein L and $L^1$ are both $-NH-$.

A fourth aspect of linking group relates to compounds having the formula:

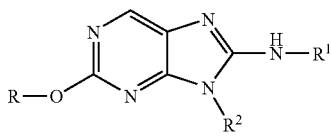

wherein L is —O— and L¹ is —NH—.

A fifth aspect of linking group relates to compounds having the formula:

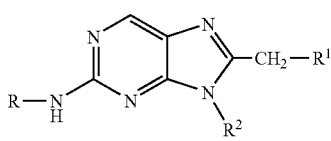

wherein L is —NH— and L¹ is —CH₂—.

A sixth aspect of linking group relates to compounds having the formula:

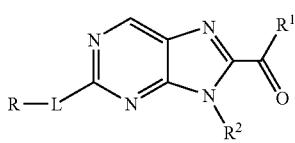

wherein L is —NH— or —O— and L¹ is —C(O)—.

Other non-limiting examples of linking units and combinations of linking units are described herein below.

The analogs (compounds) of the present invention are arranged into several categories to assist the formulator in applying a rational synthetic strategy for the preparation of analogs which are not expressly exampled herein. The arrangement into categories does not imply increased or decreased efficacy for any of the compositions of matter described herein.

The compounds of the present invention which comprise Category I are 2-[substituted or unsubstituted heterocyclic]-amino-8-[substituted or unsubstituted aryl]-amino-9-alkyl purines having the formula:

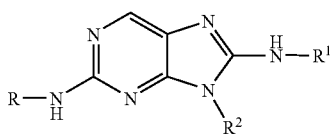

the first aspect of which relates to the R, R¹, and R² units as described herein below in Table I.

TABLE I

| No. | R | R¹ | R² |
|---|---|---|---|
| 1 | pyran-4-yl | 2-fluorophenyl | —CH₂CH₃ |
| 2 | pyran-4-yl | 4-fluorophenyl | —CH₂CH₃ |

TABLE I-continued

| No. | R | R¹ | R² |
|---|---|---|---|
| 3 | pyran-4-yl | 2-chlorophenyl | —CH₂CH₃ |
| 4 | pyran-4-yl | 2-fluoro-5-chlorophenyl | —CH₂CH₃ |
| 5 | pyran-4-yl | 2-chloro-5-fluorophenyl | —CH₂CH₃ |
| 6 | pyran-4-yl | 2,3-dichlorophenyl | —CH₂CH₃ |
| 7 | pyran-4-yl | 2-chloro-5-methylphenyl | —CH₂CH₃ |
| 8 | pyran-4-yl | 2-chloro-5-trifluoromethylphenyl | —CH₂CH₃ |
| 9 | pyran-4-yl | 2-aminophenyl | —CH₂CH₃ |
| 10 | pyran-4-yl | 2-nitrophenyl | —CH₂CH₃ |
| 11 | pyran-4-yl | 2-methoxyphenyl | —CH₂CH₃ |
| 12 | pyran-4-yl | 2-hydroxyphenyl | —CH₂CH₃ |
| 13 | pyran-4-yl | 3-methylcarboxyphenyl | —CH₂CH₃ |
| 14 | pyran-4-yl | 2,6-dichlorophenyl | —CH₂CH₃ |
| 15 | morpholin-4-yl | 2-fluorophenyl | —CH₂CH₃ |
| 16 | morpholin-4-yl | 4-fluorophenyl | —CH₂CH₃ |
| 17 | morpholin-4-yl | 2-chlorophenyl | —CH₂CH₃ |
| 18 | morpholin-4-yl | 2-fluoro-5-chlorophenyl | —CH₂CH₃ |
| 19 | morpholin-4-yl | 2-chloro-5-fluorophenyl | —CH₂CH₃ |
| 20 | morpholin-4-yl | 2,3-dichlorophenyl | —CH₂CH₃ |
| 21 | morpholin-4-yl | 2-chloro-5-methylphenyl | —CH₂CH₃ |
| 22 | morpholin-4-yl | 2-chloro-5-trifluoromethylphenyl | —CH₂CH₃ |
| 23 | morpholin-4-yl | 2-aminophenyl | —CH₂CH₃ |
| 24 | morpholin-4-yl | 2-nitrophenyl | —CH₂CH₃ |
| 25 | morpholin-4-yl | 2-methoxyphenyl | —CH₂CH₃ |
| 26 | morpholin-4-yl | 2-hydroxyphenyl | —CH₂CH₃ |
| 27 | morpholin-4-yl | 3-methylcarboxyphenyl | —CH₂CH₃ |
| 28 | morpholin-4-yl | 2,6-dichlorophenyl | —CH₂CH₃ |

The compounds which comprise the first aspect of Category I can be prepared by the procedure described herein below and outline in Scheme I.

Scheme I

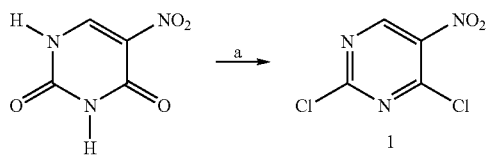

Reagents and conditions: (a) POCl₃, N,N-dimethylaniline; 150° C. 75 min.

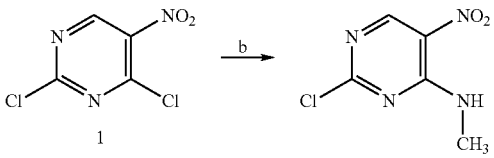

Reagents and conditions: (b) CH₃NH₂, THF; 0° C. 75 min.

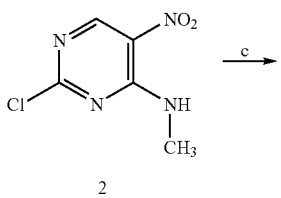

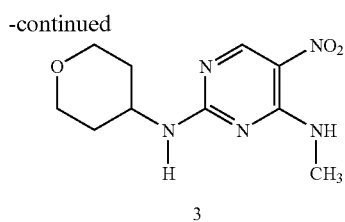

3

Reagents and conditions: (c) 4-amino tetrahydropyran; 21° C. 3 h.

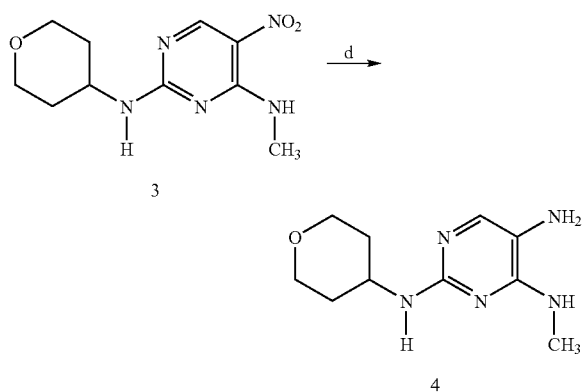

Reagents and conditions: (d) H$_2$, Pd/C, EtOH; 21° C. 1.5 h.

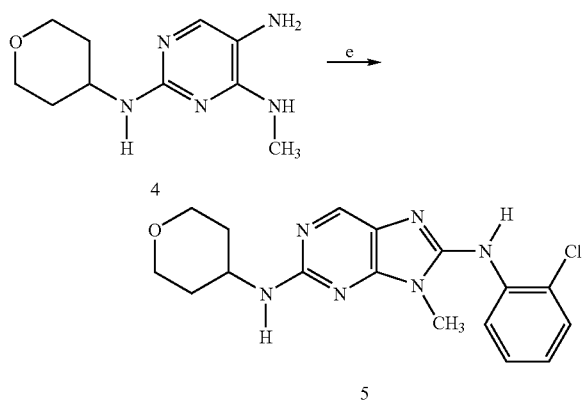

Reagents and conditions: (e) 2-chlorophenylhioisocyanate, DCM, DCC, DIPEA; rt 15 min, reflux.

EXAMPLE 1

N-8-(2-Chloro-phenyl)-9-methyl-N-2-(tetrahydro-pyran-4-yl)-9H-purine-2,8-diamine (5)

The following is the procedure for the preparation of 2,4-Dichloro-5-nitro-pyrimidine, 1. See N. Whittaker and T. S. G. Jones, *J. Chem. Soc. Abstracts, pp* 1565-1570 (1951) included herein by reference.

Preparation of 2,4-Dichloro-5-nitro-pyrimidine (1): N,N-dimethylaniline (12.1 mL, 95.5 mmol) is combined with 5-nitrouracil (10.0 g, 63.7 mmol) and stirred under a N$_2$ atmosphere. Phosphorous oxychloride (23.7 mL, 254.6 mmol) is slowly added to the stirring mixture. Upon completion of addition, the mixture is heated to 150° C. for 75 min. The reaction mixture was then poured over ice and extracted with Et$_2$O (3×250 mL). The combined organics are washed with brine, dried over MgSO$_4$ and concentrated to afford the crude product as a brown oil (6.3 g, 51%) which was further used without purification. $^1$H NMR (300 MHz, CDCl$_3$) δ 9.19 (s, 1H).

Preparation of (2-chloro-5-nitro-pyrimidin-4-yl)-methyl-amine (2): Dichloro pyrimidine, 1, (0.34 g, 1.75 mmol) is combined with THF (4 mL) and stirred in an ice/salt water bath under N$_2$ atmosphere. Methylamine (2.0 M in THF, 1.4 mL, 2.8 mmol) is added slowly to the stirring solution. After 10 minutes the mixture is diluted with H$_2$O (20 mL) and extracted with EtOAc (2×50 mL). The combined organics are dried over MgSO$_4$ and concentrated. The crude residue is purified over silica (0-10%. EtOAc/hexanes) to afford 150 mg (46% yield) or the desired product as a yellow oil. $^1$H NMR (300 MHz, CDCl$_3$) δ 9.06 (s, 1H), 8.43 (br s, 1H), 3.25 (d, J=5.1 Hz, 3H); ESI/MS: 189 (M+H).

Preparation of N-4-methyl-5-nitro-N-2-(tetrahydro-pyran-4-yl)-pyrimidine-2,4-diamine (3): 4-Amino tetrahydropyran (0.09 g, 0.88 mmol) is added to a stirred solution of (2-chloro-5-nitro-pyrimidin-4-yl)-methyl-amine, 2, (0.15 g, 0.80 mmol) in THF (5 mL). The reaction is stirred at room temperature under N$_2$ for 3 hours. The mixture is concentrated in vacuo to a crude oil which is purified over silica (10-30% EtOAc/hexane) to afford 140 mg (69% yield) of the desired product as a yellow solid. $^1$H NMR (300 MHz, CDCl$_3$) δ 8.95 (s, 1H), 8.48 (br s, 1H), 6.06 (br d, J=6.6 Hz, 1H), 4.01-4.17 (m, 3H), 3.55 (t, J=8.4 Hz, 2H), 3.13 (d, J=5.1 Hz, 3H), 2.00-2.09 (m, 2 H), 1.57-1.68 (m, 2H); ESI/MS: 254 (M+H).

Preparation of N-4-methyl-N-2-(tetrahydro-pyran-4-yl)-pyrimidine-2,4,5-triamine (4): Palladium on carbon (0.03 g) was added to a stirring solution of N-4-methyl-5-nitro-N-2-(tetrahydro-pyran-4-yl)-pyrimidine-2,4-diamine, 3, (0.14 g, 0.55 mmol) in EtOH (5 mL). A H$_2$ filled balloon was applied to the reaction flask. After 1.5 h of stirring LC/MS showed complete reaction. The mixture was filtered through celite® and concentrated to afford a yellow oil (120 mg, 98%). $^1$H NMR (300 MHz, CDCl$_3$) δ 7.44 (s, 1H), 5.64 (br s, 1H), 4.88 (br s, 1H), 3.94-3.98 (m, 3H), 3.48-3.55 (m, 2H), 3.16 (br s, 2H), 2.96 (d, J=4.8 Hz, 3H), 1.99-2.03 (m, 2H), 1.45-1.57 (m, 2H); ESI/MS: 224 (M+H).

Preparation of N-8-(2-chlorophenyl)-9-methyl-N-2-(tetrahydro-pyran-4-yl)-9H-purine-2,8-diamine (5): 2-Chlorophenyl isothiocyanate (0.03 mL, 0.25 mmol) and N,N-diisopropyl ethylamine (0.04 mL, 0.25 mmol) are added to a stirred solution of N-4-methyl-N-2-(tetrahydro-pyran-4-yl)-pyrimidine-2,4,5-triamine, 5, (0.05 g, 0.22 mmol) in 1,2-dichloroethane (4 mL). The mixture is allowed to stir at room temperature for 15 minutes then dicyclohexyl-carbodiimide (0.05 g, 0.25 mmol) is added and the mixture brought to reflux. The reaction is then diluted with H$_2$O (25 mL), and extracted twice with CH$_2$Cl$_2$ (50 mL). The combined organic layers are dried over MgSO$_4$ and concentrated to a residue which is purified prep HPLC chromatography to affore 38 mg (48% yield) of the desired product as white solid. $^1$H NMR (300 MHz, CDCl$_3$) δ 8.60 (d, J=8.1 Hz, 1H), 8.42 (s, 1H), 7.36-7.46 (m, 2H), 7.01-7.07 (m, 1H), 6.99 (br s, 1H), 5.06 (d, J=7.8 Hz, 1H), 4.01-4.19 (m, 3H), 3.68 (s, 3H), 3.61 (dt, J=11.4, 2.1 Hz, 2 H), 2.07-2.20 (m, 2H), 1.54-1.64 (m, 2H); ESI/MS: 359 (M+H).

The following is a further non-limiting example of the first aspect of Category I.

N-8-(4-Fluorophenyl)-9-methyl-N-2-(tetrahydro-pyran-4-yl)-9H-purine-2,8-diamine: $^1$H NMR (300 MHz, CDCl$_3$) δ 8.36 (s, 1H), 7.55-7.60 (m, 2H), 7.10 (t, J=8.7 Hz, 2H), 6.30 (br s, 1H), 4.93 (d, J=7.8 Hz, 1H), 4.00-4.12 (m, 3H), 3.55-3.64 (m, 5H), 2.08-2.13 (m, 2H), 1.52-1.65 (m, 2H); ESI/MS: 343 (M+H).

The compounds of the present invention which comprise the second aspect of Category I are 2-[substituted or unsubstituted aryl]-amino-8-[substituted or unsubstituted aryl]-amino-9-alkyl purines having the formula:

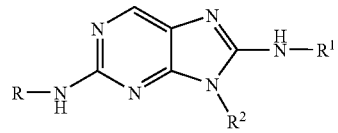

wherein R, R$^1$, and R$^2$ units as described herein below in Table II.

TABLE II

| No. | R | R$^1$ | R$^2$ |
|---|---|---|---|
| 29 | 2,6-difluorophenyl | 2-fluorophenyl | —CH$_2$CH$_3$ |
| 30 | 2,6-difluorophenyl | 4-fluorophenyl | —CH$_2$CH$_3$ |
| 31 | 2,6-difluorophenyl | 2-chlorophenyl | —CH$_2$CH$_3$ |
| 32 | 2,6-difluorophenyl | 2-fluoro-5-chlorophenyl | —CH$_2$CH$_3$ |
| 33 | 2,6-difluorophenyl | 2-chloro-5-fluorophenyl | —CH$_2$CH$_3$ |
| 34 | 2,6-difluorophenyl | 2,3-dichlorophenyl | —CH$_2$CH$_3$ |
| 35 | 2,6-difluorophenyl | 2-chloro-5-methylphenyl | —CH$_2$CH$_3$ |
| 36 | 2,6-difluorophenyl | 2-chloro-5-trifluoromethylphenyl | —CH$_2$CH$_3$ |
| 37 | 2,6-difluorophenyl | 2-aminophenyl | —CH$_2$CH$_3$ |
| 38 | 2,6-difluorophenyl | 2-nitrophenyl | —CH$_2$CH$_3$ |
| 39 | 2,6-difluorophenyl | 2-methoxyphenyl | —CH$_2$CH$_3$ |
| 40 | 2,6-difluorophenyl | 2-hydroxyphenyl | —CH$_2$CH$_3$ |
| 41 | 2,6-difluorophenyl | 3-methylcarboxyphenyl | —CH$_2$CH$_3$ |
| 42 | 2,6-difluorophenyl | 2,6-dichlorophenyl | —CH$_2$CH$_3$ |
| 43 | 2,4-difluorophenyl | 2-fluorophenyl | —CH$_2$CH$_3$ |
| 44 | 2,4-difluorophenyl | 4-fluorophenyl | —CH$_2$CH$_3$ |
| 45 | 2,4-difluorophenyl | 2-chlorophenyl | —CH$_2$CH$_3$ |
| 46 | 2,4-difluorophenyl | 2-fluoro-5-chlorophenyl | —CH$_2$CH$_3$ |
| 47 | 2,4-difluorophenyl | 2-chloro-5-fluorophenyl | —CH$_2$CH$_3$ |
| 48 | 2,4-difluorophenyl | 2,3-dichlorophenyl | —CH$_2$CH$_3$ |
| 49 | 2,4-difluorophenyl | 2-chloro-5-methylphenyl | —CH$_2$CH$_3$ |
| 50 | 2,4-difluorophenyl | 2-chloro-5-trifluoromethylphenyl | —CH$_2$CH$_3$ |
| 51 | 2,4-difluorophenyl | 2-aminophenyl | —CH$_2$CH$_3$ |
| 52 | 2,4-difluorophenyl | 2-nitrophenyl | —CH$_2$CH$_3$ |
| 53 | 2,4-difluorophenyl | 2-methoxyphenyl | —CH$_2$CH$_3$ |
| 54 | 2,4-difluorophenyl | 2-hydroxyphenyl | —CH$_2$CH$_3$ |
| 55 | 2,4-difluorophenyl | 3-methylcarboxyphenyl | —CH$_2$CH$_3$ |
| 56 | 2,4-difluorophenyl | 2,6-dichlorophenyl | —CH$_2$CH$_3$ |

The compounds which comprise the second aspect of Category I can be prepared by the procedure described herein below as outlined in Scheme II. Intermediate 6 can be prepared by the same procedure as intermediate 2 described herein above, by substituting ethylamine for methylamine.

Scheme II

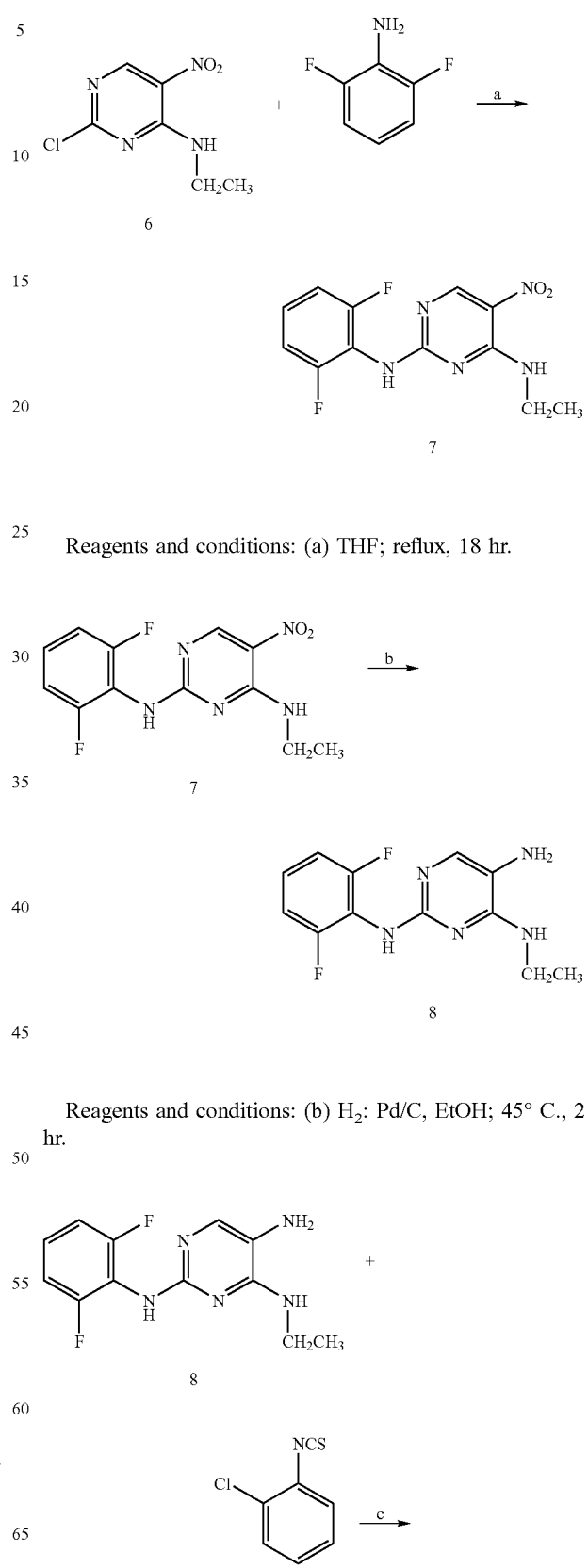

Reagents and conditions: (a) THF; reflux, 18 hr.

Reagents and conditions: (b) H$_2$: Pd/C, EtOH; 45° C., 2 hr.

-continued

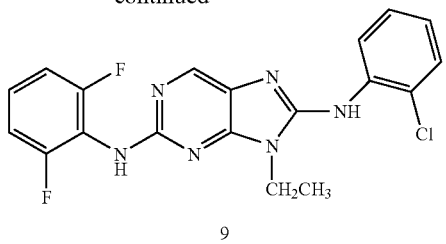

9

Reagents and conditions: (c) DIPEA, DCC, $CH_2ClCH_2Cl$; reflux, 2 hr.

EXAMPLE 2

N-8-(2-Chlorophenyl)-N-2-(2,6-difluorophenyl)-9-ethyl-9H-purine-2,8-diamine (9)

Preparation of N-2-(2,6-Difluorophenyl)-N-4-ethyl-5-nitro-pyrimidine-2,4-diamine (7): 2,6-Difluorophenyl aniline (0.64 mL, 5.9 mmol) is added to a solution of (2-chloro-5-nitro-pyrimidin-4-yl)-ethyl-amine, 6, (0.3 g, 1.49 mmol) in THF (10 mL). The reaction is heated to reflux under $N_2$ for 18 hours (LC/MS indicated complete reaction). The mixture is concentrated in vacuo and the residue purified over silica (gradient 7-15% EtOAc/hexane) to afford 210 mg (48% yield) of the desired product as a yellow solid. $^1$H NMR (300 MHz, $CDCl_3$) δ 9.03 (s, 1H), 8.40 (br s, 1H), 7.23-7.31 (m, 1H), 7.04 (t, J=8.1 Hz, 2H), 3.45 (br t, J=6.6 Hz, 2H), 1.21 (t, J=7.2 Hz, 3H); ESI/MS: 296 (M+H).

Preparation of N-2-(2,6-difluorophenyl)-N-4-ethyl-pyrimidine-2,4,5-triamine (8): Palladium on carbon (0.03 g) is added to a solution of N-2-(2,6-difluorophenyl)-N-4-ethyl-5-nitro-pyrimidine-2,4-diamine, 7, (0.20 g, 0.62 mmol) in EtOH (10 mL). A $H_2$ balloon is applied to the reaction flask and the mixture warmed to 45° C. After 2 hours LC/MS indicates the reaction is complete and the mixture is filtered through celite®, concentrated in vacuo to afford the desired product which is used without further purification. $^1$H NMR (300 MHz, $CDCl_3$) δ 10.33 (br s, 1H), 9.08 (s, 1H), 7.54-7.58 (m, 2H), 7.10-7.15 (m, 2H), 6.17 (br d J=8.7 Hz, 1H), 3.88-3.98 (m, 1H), 1.23-1.31 (overlapping d's, 9H), minor isomer: 10.27 (br s, 1H), 9.12 (s, 1H), 7.54-7.58 (m, 2H), 7.10-7.15 (m, 2H), 5.82 (br d J=8.4 Hz, 1H), 4.21-4.27 (m, 1H), 1.23-1.31 (overlapping d's, 9H); ESI/MS: 306 (M+H).

Preparation of N-8-(2-chlorophenyl)-N-2-(2,6-difluorophenyl)-9-ethyl-9H-purine-2,8-diamine (9): 2-Chlorophenyl isothiocyanate (0.05 mL, 0.42 mmol) followed by DIPEA (0.07 mL, 0.42 mmol) is added to a solution of N-2-(2,6-difluorophenyl)-N-4-ethyl-pyrimidine-2,4,5-triamine, 8, (0.1 g, 0.38 mmol) in 1,2-dichloroethane (5 mL). The mixture is allowed to stir at room temperature for 15 minutes then dicyclohexylcarbodiimide (0.09 g, 0.42 mmol) is added and the mixture heated to reflux for 2 hours. The reaction is cooled and diluted with $H_2O$ (50 mL) and extracted with $CH_2Cl_2$. The combined organic layers are dried over $MgSO_4$, concentrated in vacuo and the resulting crude residue is purified over silica (30% EtOAc/hexane) to afford 83 mg (55% yield) of the desired product as a yellow solid. $^1$H NMR (300 MHz, $CDCl_3$) δ 8.63 (d, J=8.1 Hz, 1H), 8.51 (s, 1H), 7.36-7.45 (m, 2H), 7.12-7.22 (m, 1H), 6.98-7.06 (m, 4 H), 6.91 (br s, 1H), 4.14 (q, J=7.2 Hz, 2H), 1.49 (t, J=7.2 Hz, 3H). ESI/MS: 401 (M+H).

The following are non-limiting examples of compounds which comprise the second aspect of Category I.

N-8-(2-Chlorophenyl)-N-2-(4-fluorophenyl)-9-ethyl-9H-purine-2,8-diamine: $^1$H NMR (300 MHz, DMSO) δ 8.63 (s, 1H), 8.37 (s, 1H), 8.02 (d, J=8.1 Hz, 1H), 7.85 (dd, J=9.0, 5.1 Hz, 2H), 7.54 (d, J=8.1 Hz, 1H), 7.38 (t, J=8.1 Hz, 1H), 7.08-7.20 (m, 3H), 3.69 (s, 3H). ESI/MS: 369 (M+H).

N-8-(2-Chlorophenyl)-N-2-(2,4-difluorophenyl)-9-methyl-9H-purine-2,8-diamine: $^1$H NMR (300 MHz, $CDCl_3$) δ 8.65 (d, J=8.1 Hz, 1H), 8.49-8.58 (m, 2H), 7.38-7.46 (m, 2H), 7.18 (br s, 1H), 7.06 (dt, J=7.8, 1.2 Hz, 2H), 6.88-6.96 (m, 2H), 3.74 (s, 3H). ESI/MS: 387 (M+H) Anal. calcd for $C_{18}H_{13}ClF_2N_6$ (0.1$H_2O$): C, 55.64; H, 3.42; N, 21.63. Found: C, 55.70; H, 2.94; N, 21.13.

N-8-(2-Chlorophenyl)-N-2-(2,4-difluorophenyl)-9-methyl-9H-purine-2,8-diamine: $^1$H NMR (300 MHz, $CDCl_3$) δ 8.60-8.67 (m, 2H), 8.56 (s, 1H), 7.36-7.46 (m, 3H), 6.95-7.22 (m, 5H), 4.24 (q, J=7.2 Hz, 2H), 1.57 (t, J=7.2 Hz, 3H); ESI/MS: 383 (M+H).

N-8-(2-Chlorophenyl)-N-2-(2,6-difluorophenyl)-9-isopropyl-9H-purine-2,8-diamine: $^1$H NMR (300 MHz, $CDCl_3$) δ 8.61 (d, J=8.1 Hz, 1H), 8.51 (s, 1H), 7.36-7.45 (m, 2H), 7.12-7.22 (m, 1H), 7.09 (br s, 1H), 6.97-7.06 (m, 3H), 6.71 (br s, 1H), 4.73 (sep, J=6.9 Hz, 1H), 1.69 (d, J=7.2 Hz, 6H); ES/MS: 415 (M+H).

N-8-(2-Chlorophenyl)-N-2-(2,6-difluorophenyl)-9H-purine-2,8-diamine: $^1$H NMR (300 MHz, $CDCl_3$) δ 9.41 (br s, 1H), 7.97 (s, 1H), 7.81 (d, J=8.1 Hz, 1H), 7.41 (dd, J=9.3, 1.5 Hz, 1H), 7.17-7.29 (m, 5H), 6.92 (t overlapping br s, J=8.1, 2H); $^{19}$F NMR (282 MHz, $CDCl_3$) δ 45.47 (s, 2 F); HRMS (FAB) calc. for $C_{17}H_{12}N_6F_2Cl$: 373.0780 found 373.0776 (M+H).

3-[8-(2-Chlorophenylamino)-2-(2,6-difluorophenylamino)-purin-9-yl]-(S)-2-methyl-butan-2-ol: $^1$H NMR (300 MHz, $CDCl_3$) δ 8.50 (br s, 1H), 8.14 (s, 1H), 6.99-7.45 (m, 8H), 4.58 (m, 1H), 1.63 (d, J=7.5 Hz, 3H), 1.24-1.27 (overlapping d's, 6H); HRMS (FAB) calc. for $C_{22}H_{22}N_6OF_2Cl$: 459.1511 found 459.1493 (M+H).

9-Butyl-N-8-(2-chloro-phenyl)-N-2-(2,6-difluoro-phenyl)-9H-purine-2,8-diamine: $^1$H NMR (300 MHz, $CDCl_3$) δ 8.64 (d, J=8.1 Hz, 1H), 8.51 (s, 1H), 7.34-7.43 (m, 2H), 7.26 (br s, 1H), 6.9.6-7.04 (m, 3H), 4.06 (t, J=7.2 Hz, 2H), 1.81-1.89 (m, 2H), 1.36-1.45 (m, 2H), 0.97 (t, J=7.2 Hz, 3H); ESI/MS: 429 (M+H).

N-8-(2-Chlorophenyl)-9-cyclopropyl-N-2-(2,6-difluorophenyl)-9H-purine-2,8-diamine: $^1$H NMR (300 MHz, $CDCl_3$) δ 8.77 (d, J=8.1 Hz, 1H), 8.47 (s, 1H), 7.77 (s, 1H), 7.38-7.46 (m, 2H), 7.14-7.24 (m, 1H), 6.99-7.07 (m, 3H), 6.74 (br s, 1H), 3.01-3.08 (m, 1H), 1.27-1.33 (m, 4H); ESI/MS: 413 (M+H).

9-tert-Butyl-N-8-(2-chlorophenyl)-N-2-(2,6-difluorophenyl)-9H-purine-2,8-diamine: $^1$H NMR (300 MHz, $CDCl_3$) δ 8.59 (d, J=8.4 Hz, 1H), 8.51 (s, 1H), 7.46 (br s, 1H), 7.34-7.44 (m, 2H), 7.11-7.21 (m, 1H), 6.96-7.03 (m, 3H), 6.68 (br s, 1H), 1.91 (s, 9H); ESI/MS: 429 (M+H).

N-8-(2-Chloro-4-fluoro-phenyl)-N-2-(2,6-difluoro-phenyl)-9-ethyl-9H-purine-2,8-diamine: $^1$H NMR (300 MHz, $CDCl_3$) δ 8.60-8.65 (m, 1H), 8.48 (s, 1H), 7.09-7.23 (m, 3H), 6.99-7.06 (m, 2H), 6.88 (br s, 1H), 6.81 (br s, 1H), 4.13 (q, J=7.2 Hz, 2H), 1.50 (t, J=7.2 Hz, 3H); ESI/MS: 419 (M+H).

N-8-(2-Chlorophenyl)-N-2-(2,6-difluorophenyl)-9-methyl-9H-purine-2,8-diamine: $^1$H NMR (300 MHz, $CDCl_3$) δ 8.47 (dd, J=8.1, 1.2 Hz, 1H), 8.34 (s, 1H), 7.42-7.51 (dt overlapping dd, J=8.1, 1.2 Hz; 8.1, 1.2 Hz 2H), 7.27-7.37 (m, 3H), 7.20 (dd, J=7.8, 1.2 Hz, 1H), 7.04 (br t app, J=8.4

Hz, 2H), 3.61 (s, 3H); $^{19}$F NMR (CDCl$_3$) δ 46.19 (br s, 2 F); HRMS (FAB) calc. for C$_{18}$H$_{14}$N$_6$F$_2$Cl: 387.0936 found 387.0947 (M+H).

The compounds of the present invention which comprise the third aspect of Category I are 2-[substituted or unsubstituted alkyl]-amino-8-[substituted or unsubstituted aryl]-amino-9-alkyl purines having the formula:

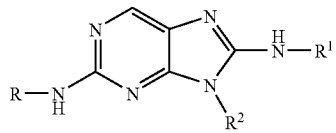

wherein R, R$^1$, and R$^2$ units as described herein below in Table III.

TABLE III

| No. | R | R$^1$ | R$^2$ |
|---|---|---|---|
| 57 | 2-methyl-2-hydroxy-1-(S)-methylpropyl | 2-fluorophenyl | ethyl |
| 58 | 2-methyl-2-hydroxy-1-(S)-methylpropyl | 4-fluorophenyl | ethyl |
| 59 | 2-methyl-2-hydroxy-1-(S)-methylpropyl | 2-chlorophenyl | ethyl |
| 60 | 2-methyl-2-hydroxy-1-(S)-methylpropyl | 2-fluoro-5-chlorophenyl | ethyl |
| 61 | 2-methyl-2-hydroxy-1-(S)-methylpropyl | 2-chloro-5-fluorophenyl | ethyl |
| 62 | 2-methyl-2-hydroxy-1-(S)-methylpropyl | 2,3-dichlorophenyl | ethyl |
| 63 | 2-methyl-2-hydroxy-1-(S)-methylpropyl | 2-chloro-5-methylphenyl | ethyl |
| 64 | 2-methyl-2-hydroxy-1-(S)-methylpropyl | 2-chloro-5-trifluoromethylphenyl | ethyl |
| 65 | 2-methyl-2-hydroxy-1-(S)-methylpropyl | 2-aminophenyl | ethyl |
| 66 | 2-methyl-2-hydroxy-1-(S)-methylpropyl | 2-nitrophenyl | ethyl |
| 67 | 2-methyl-2-hydroxy-1-(S)-methylpropyl | 2-methoxyphenyl | ethyl |
| 68 | 2-methyl-2-hydroxy-1-(S)-methylpropyl | 2-hydroxyphenyl | ethyl |
| 69 | 2-methyl-2-hydroxy-1-(S)-methylpropyl | 3-methylcarboxyphenyl | ethyl |
| 70 | 2-methyl-2-hydroxy-1-(S)-methylpropyl | 2,6-dichlorophenyl | ethyl |
| 71 | 2-methoxy-1-(S)-methylethyl | 2-fluorophenyl | ethyl |
| 72 | 2-methoxy-1-(S)-methylethyl | 4-fluorophenyl | ethyl |
| 73 | 2-methoxy-1-(S)-methylethyl | 2-chlorophenyl | ethyl |
| 74 | 2-methoxy-1-(S)-methylethyl | 2-fluoro-5-chlorophenyl | ethyl |
| 75 | 2-methoxy-1-(S)-methylethyl | 2-chloro-5-fluorophenyl | ethyl |
| 76 | 2-methoxy-1-(S)-methylethyl | 2,3-dichlorophenyl | ethyl |
| 77 | 2-methoxy-1-(S)-methylethyl | 2-chloro-5-methylphenyl | ethyl |
| 78 | 2-methoxy-1-(S)-methylethyl | 2-chloro-5-trifluoromethylphenyl | ethyl |
| 79 | 2-methoxy-1-(S)-methylethyl | 2-aminophenyl | ethyl |
| 80 | 2-methoxy-1-(S)-methylethyl | 2-nitorphenyl | ethyl |
| 81 | 2-methoxy-1-(S)-methylethyl | 2-methoxyphenyl | ethyl |
| 82 | 2-methoxy-1-(S)-methylethyl | 2-hydroxyphenyl | ethyl |
| 83 | 2-methoxy-1-(S)-methylethyl | 3-methylcarboxyphenyl | ethyl |
| 84 | 2-methoxy-1-(S)-methylethyl | 2,6-dichlorophenyl | ethyl |
| 85 | 1-(S)-methylpropyl | 2-fluorophenyl | ethyl |
| 86 | 1-(S)-methylpropyl | 4-fluorophenyl | ethyl |
| 87 | 1-(S)-methylpropyl | 2-chlorophenyl | ethyl |
| 88 | 1-(S)-methylpropyl | 2-fluoro-5-chlorophenyl | ethyl |
| 89 | 1-(S)-methylpropyl | 2-chloro-5-fluorophenyl | ethyl |
| 90 | 1-(S)-methylpropyl | 2,3-dichlorophenyl | ethyl |
| 91 | 1-(S)-methylpropyl | 2-chloro-5-methylphenyl | ethyl |
| 92 | 1-(S)-methylpropyl | 2-chloro-5-trifluoromethylphenyl | ethyl |
| 93 | 1-(S)-methylpropyl | 2-aminophenyl | ethyl |
| 94 | 1-(S)-methylpropyl | 2-nitorphenyl | ethyl |
| 95 | 1-(S)-methylpropyl | 2-methoxyphenyl | ethyl |
| 96 | 1-(S)-methylpropyl | 2-hydroxyphenyl | ethyl |
| 97 | 1-(S)-methylpropyl | 3-methylcarboxyphenyl | ethyl |
| 98 | 1-(S)-methylpropyl | 2,6-dichlorophenyl | ethyl |

The compounds which comprise the third aspect of Category I can be prepared according to the procedure for the first and second aspects of the present invention, as described herein above.

The following are non-limiting examples of compounds which comprise the third aspect of Category I.

3-[8-(2-Chlorophenylamino)-9-methyl-9H-purin-2-ylamino]-2-methyl-butan-2-ol: $^1$H NMR (300 MHz, CDCl$_3$) δ 8.59 (d, J=8.1 Hz, 1H), 8.34 (s, 1H), 7.37-7.46 (m, 2H), 7.02-7.08 (m, 2H), 5.48 (br s, 1H), 4.06-4.16 (m, 1H), 3.68 (s, 3H), 1.28-1.34 (m, 9H); ESI/MS: 361 (M+H).

The compounds of the present invention which comprise Category II are 2-[substituted or unsubstituted aryl]-oxy-8-[substituted or unsubstituted aryl]-amino-9-alkyl purines having the formula:

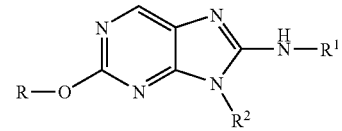

the first aspect of which relates to the R, R$^1$, and R$^2$ units as described herein below in Table IV.

TABLE IV

| No. | R | R$^1$ | R$^2$ |
|---|---|---|---|
| 99 | 2,6-difluorophenyl | 2-fluorophenyl | —CH$_2$CH$_3$ |
| 100 | 2,6-difluorophenyl | 4-fluorophenyl | —CH$_2$CH$_3$ |
| 101 | 2,6-difluorophenyl | 2-chlorophenyl | —CH$_2$CH$_3$ |
| 102 | 2,6-difluorophenyl | 2-fluoro-5-chlorophenyl | —CH$_2$CH$_3$ |
| 103 | 2,6-difluorophenyl | 2-chloro-5-fluorophenyl | —CH$_2$CH$_3$ |
| 104 | 2,6-difluorophenyl | 2,3-dichlorophenyl | —CH$_2$CH$_3$ |
| 105 | 2,6-difluorophenyl | 2-chloro-5-methylphenyl | —CH$_2$CH$_3$ |
| 106 | 2,6-difluorophenyl | 2-chloro-5-trifluoromethylphenyl | —CH$_2$CH$_3$ |
| 107 | 2,6-difluorophenyl | 2-aminophenyl | —CH$_2$CH$_3$ |
| 108 | 2,6-difluorophenyl | 2-nitrophenyl | —CH$_2$CH$_3$ |
| 109 | 2,6-difluorophenyl | 2-methoxyphenyl | —CH$_2$CH$_3$ |
| 110 | 2,6-difluorophenyl | 2-hydroxyphenyl | —CH$_2$CH$_3$ |
| 111 | 2,6-difluorophenyl | 3-methylcarboxyphenyl | —CH$_2$CH$_3$ |
| 112 | 2,6-difluorophenyl | 2,6-dichlorophenyl | —CH$_2$CH$_3$ |
| 113 | 2-fluorophenyl | 2-fluorophenyl | —CH$_2$CH$_3$ |
| 114 | 2-fluorophenyl | 4-fluorophenyl | —CH$_2$CH$_3$ |
| 115 | 2-fluorophenyl | 2-chlorophenyl | —CH$_2$CH$_3$ |
| 116 | 2-fluorophenyl | 2-fluoro-5-chlorophenyl | —CH$_2$CH$_3$ |
| 117 | 2-fluorophenyl | 2-chloro-5-fluorophenyl | —CH$_2$CH$_3$ |
| 118 | 2-fluorophenyl | 2,3-dichlorophenyl | —CH$_2$CH$_3$ |
| 119 | 2-fluorophenyl | 2-chloro-5-methylphenyl | —CH$_2$CH$_3$ |
| 120 | 2-fluorophenyl | 2-chloro-5-trifluoromethylphenyl | —CH$_2$CH$_3$ |
| 121 | 2-fluorophenyl | 2-aminophenyl | —CH$_2$CH$_3$ |
| 122 | 2-fluorophenyl | 2-nitrophenyl | —CH$_2$CH$_3$ |
| 123 | 2-fluorophenyl | 2-methoxyphenyl | —CH$_2$CH$_3$ |
| 124 | 2-fluorophenyl | 2-hydroxyphenyl | —CH$_2$CH$_3$ |
| 125 | 2-fluorophenyl | 3-methylcarboxyphenyl | —CH$_2$CH$_3$ |
| 126 | 2-fluorophenyl | 2,6-dichlorophenyl | —CH$_2$CH$_3$ |

The compounds which comprise the first aspect of Category II can be prepared by the procedure described herein below as outlined in Scheme II. Intermediate 6 can be prepared by the same procedure as intermediate 2 described herein above, by substituting ethylamine for methylamine.

Scheme III

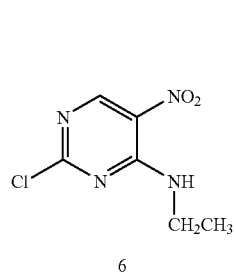

6

Reagents and conditions: (a) DIPEA; 130° C., 3 hr.

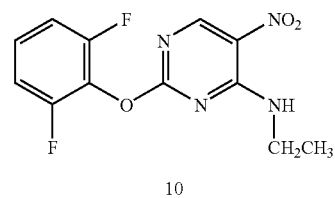

10

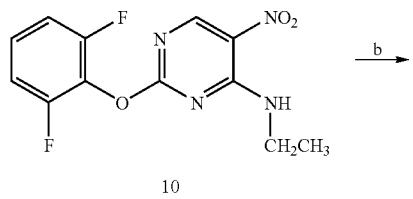

11

Reagents and conditions: (b) H$_2$, Pd/C, EtOH; 45° C., 2 hr.

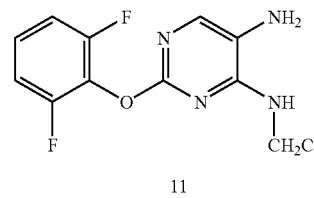

11

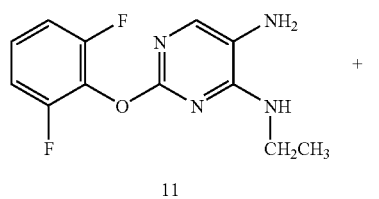

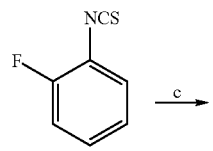

-continued

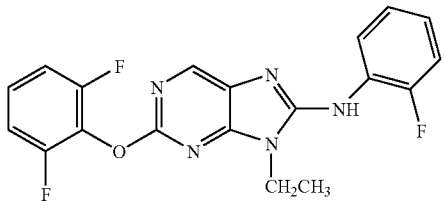

12

Reagents and conditions: (c) DCC, 1,2-dichloroethane; reflux, 2 hr.

EXAMPLE 3

[2-(2,6-Difluoro-phenoxy)-9-ethyl-9H-purin-8-yl]-(2-fluoro-phenyl)-amine (12)

Preparation of [2-(2,6-difluorophenoxy)-5-nitro-pyrimidin-4-yl]-ethyl-amine (10): 2,6-Difluorophenol (2.1 g, 16.1 mmol) is added to a solution of (2-chloro-5-nitro-pyrimidin-4-yl)-ethyl-amine, 6, (3.0 g, 14.9 mmol) in N,N-diisopropyl ethylamine (50 mL). The reaction is heated to reflux (~130° C.) under N$_2$ for 3 hours at which point monitoring of the reaction via LC/MS indicates the starting material is consumed. The mixture is diluted with 1 N HCl (500 mL) and the resulting mixture extracted three times with EtOAc (500 mL). The organic layers are combined, dried over MgSO$_4$ and concentrated in vacuo to an oil which is purified over silica (15% EtOAc/hexane) to afford 3.2 g (73% yield) of the desired product as a yellow oil. $^1$H NMR (300 MHz, CDCl$_3$) δ 9.07 (s, 1H), 8.43 (br s, 1H), 7.13-7.23 (m, 1H), 6.98 (t, J=7.8 Hz, 2H), 3.44-3.53 (m, 2H), 1.22 (t, J=7.2 Hz, 3H); ESI/MS: 297 (M+H).

Preparation of 2-(2,6-difluorophenoxy)-N-4-ethyl-pyrimidine-4,5-diamine (11): Palladium on carbon (0.4 g) is added to a stirred solution of [2-(2,6-difluorophenoxy)-5-nitro-pyrimidin-4-yl]-ethyl-amine, 10, (3.2 g, 10.8 mmol) in EtOH (60 mL). A balloon containing hydrogen is applied to the reaction flask and the mixture warmed to 45° C. After 2 hours analysis via LC/MS indicates the starting material has been consumed. The mixture is filtered through Celite® to remove the catalyst and the filtrated concentrated in vacuo to afford 2.8 g (99% yield) of the desired product as a yellow oil. $^1$H NMR (300 MHz, CDCl$_3$) δ 7.07-7.31 (m, 4H), 6.93 (br s, 1H), 3.22-3.31 (m, 4H), 1.10 (t, J=7.2 Hz, 3H); ESI/MS: 267 (M+H).

Preparation of [2-(2,6-difluorophenoxy)-9-ethyl-9H-purin-8-yl]-(2-fluorophenyl)-amine (12): 2-Fluorophenyl isothiocyanate (0.09 mL, 0.6 mmol) and DIPEA (0.07 mL, 0.41 mmol) are added to a solution of 2-(2,6-difluorophenoxy)-N-4-ethyl-pyrimidine-4,5-diamine, 11, (0.1 g, 0.38 mmol) in 1,2-dichloroethane (5 mL). The mixture is stirred at room temperature for 15 minutes after which time dicyclohexycarbodiimide (0.08 g, 0.41 mmol) is added and the mixture refluxed for 2 hours. The mixture is then diluted with H$_2$O (50 mL), extracted three times with CH$_2$Cl$_2$ (50 mL) and the combined organic layers are dried over MgSO$_4$ and concentrated in vacuo to a residue which id purified over silica (30% EtOAc/hexane) to afford 30 mg (18% yield) of the desired product as a yellow solid. $^1$H NMR (300 MHz, CDCl$_3$) δ 8.54 (t, J=7.8 Hz, 1H), 8.48 (s, 1H), 7.03-7.26 (m, 6H), 6.68 (br s, 1H), 4.25 (q, J=7.2 Hz, 2H), 1.53 (t, J=7.2 Hz, 3H); ESI/MS: 386 (M+H).

[2-(2,6-Difluoro-phenoxy)-9-ethyl-9H-purin-8-yl]-o-tolyl-amine $^1$H NMR (300 MHz, CDCl$_3$) δ 8.40 (s, 1H), 7.92 (d, J=8.1 Hz, 1H), 7.11-7.34 (m, 5H), 7.05 (t, J=7.8 Hz, 2H), 4.21 (q, J=7.2 Hz, 2H), 2.38 (s, 3H), 1.51 (t, J=7.2 Hz, 3H); ESI/MS: 382 (M+H).

(2-Chloro-phenyl)-[2-(2,6-difluoro-phenoxy)-9-ethyl-9H-purin-8-yl]-amine: $^1$H NMR (300 MHz, CDCl$_3$) δ 8.66 (br d, J=7.8 Hz 1H), 8.50 (s, 1H), 7.03-7.48 (m, 7H), 4.28 (q, J=7.5 Hz, 2H), 1.56 (t, J=7.5 Hz, 3H); $^{19}$F NMR (282 MHz, CDCl$_3$) δ 36.88 (t, J=6.2 Hz, 2 F); HRMS (FAB) calc. for C$_{19}$H$_{15}$N$_5$OF$_2$Cl: 402.0933 found 402.0924 (M+H).

(2-Chlorophenyl)-[2-(2,6-difluoro-4-methylaminomethyl-phenoxy)-9-ethyl-9H-purin-8-yl]-amine: $^1$H NMR (300 MHz, CD$_3$OD) δ 8.24 (s, 1H), 7.71 (dd, J=7.5, 1.8 Hz, 1H), 7.64 (dd, J=7.8, 1.5 Hz, 1H), 7.32-7.52 (m, 4H), 4.32 (q, J=7.2 Hz, 2H), 4.27 (s, 3H), 2.80 (s, 3H), 1.50 (t, J=7.2 Hz, 3H); $^{19}$F NMR (282 MHz, CD$_3$OD) δ 36.47 (d, J=7.6 Hz, 2 F); HRMS (FAB) calc. for C$_{21}$H$_{19}$N$_6$OF$_2$Cl: 445.1355 found 445.1339 (M+H).

[2-(2,6-Difluorophenoxy)-9-ethyl-9H-purin-8-yl]-(2-nitrophenyl)-amine: $^1$H NMR (300 MHz, CDCl$_3$) δ 9.21 (dd, J=8.4, 1.5 Hz, 1H), 8.57 (s, 1H), 8.36 (dd, J=8.4, 1.5 Hz, 1H), 7.79 (dt, J=8.1, 1.5 Hz, 1H), 7.14-7.25 (m, 2H), 7.06 (t, J=7.5 hz, 2H), 4.34 (q, J=7.2 Hz, 2H), 1.57 (t, J=7.2 Hz, 3H); ESI/MS: 413 (M+H).

N-[2-(2,6-Difluorophenoxy)-9-ethyl-9H-purin-8-yl]-benzene-1,2-diamine: $^1$H NMR (300 MHz, CDCl$_3$) δ 8.33 (s, 1H), 7.45 (dd, J=8.1, 1.5 Hz, 1H), 7.02-7.23 (m, 4H), 6.86-6.92 (m, 2H), 4.20 (q, J=7.2 Hz, 2H), 1.48 (t, J=7.2 Hz, 3H); ESI/MS: 383 (M+H).

4-[8-(2-Chlorophenylamino)-9-ethyl-9H-purin-2-yloxy]-3,5-difluoro-N-methyl-benzamide: $^1$H NMR (300 MHz, CDCl$_3$) δ 8.24 (br d, J=8.7, Hz 1H), 8.48 (s, 1H), 7.39-7.51 (m, 4H), 7.10 (dt, J=7.8, 1.5 Hz, 1H), 6.13 (br d app, J=4.2 Hz, 1H), 4.25 (q, J=7.2 Hz, 2H), 3.06 (d, J=4.8 Hz, 3H), 1.54 (t, J=7.2 Hz, 3H); $^{19}$F NMR (282 MHz, CDCl$_3$) δ 39.43 (d, J=7.6 Hz, 2 F); HRMS (FAB) calc. for C$_{21}$H$_{17}$N$_6$O$_2$F$_2$Cl: 459.1147 found 459.1144 (M+H).

(2-Chlorophenyl)-[9-ethyl-2-(2-fluoro-phenoxy)-9H-purin-8-yl]-amine: $^1$H NMR (300 MHz, CDCl$_3$) δ 8.66 (d, J=8.1 Hz, 1H), 8.51 (s, 1H), 7.31-7.47 (m, 3H), 7.20-7.26 (m, 3H), 7.19 (br s, 1H), 7.04-7.10 (m, 1H), 4.27 (q, J=7.2 Hz, 2H), 1.55 (t, J=7.2 Hz, 3H); ESI/MS: 384 (M+H).

(2-Chloro-5-fluorophenyl)-[2-(2,6-difluorophenoxy)-9-ethyl-9H-purin-8-yl]-amine: $^1$H NMR (300 MHz, CDCl$_3$) δ 8.64 (dd, J=10.8, 3.0 Hz, 1H), 8.53 (s, 1H), 7.38-7.43 (m, 1H), 7.17-7.25 (m, 2H), 7.03-7.08 (m, 2H), 6.76-6.83 (m, 1H), 4.27 (q, J=7.2 Hz, 2H), 1.56 (t, J=7.2 Hz, 3H); ESI/MS: 419 (M+H).

(2-Chloro-5-methylphenyl)-[2-(2,6-difluorophenoxy)-9-ethyl-9H-purin-8-yl]-amine: $^1$H NMR (300 MHz, CDCl$_3$) δ 8.50 (s, 1H), 8.45 (s, 1H), 7.32 (d, J=8.4 Hz, I H), 7.16-7.24 (m, 2H), 7.02-7.08 (m, 3H), 6.88 (dd, J=8.1, 1.5 Hz, 1H), 4.25 (q, J=7.2 Hz, 2H), 2.44 (s, 3H), 1.54 (t, J=7.2 Hz, 3H); ESI/MS: 416 (M+H).

(2,3-Dichlorophenyl)-[2-(2,6-difluorophenoxy)-9-ethyl-9H-purin-8-yl]-amine: $^1$H NMR (300 MHz, CDCl$_3$) δ 8.65 (d, J=8.1 Hz, 1H), 8.51 (s, 1H), 7.34 (t, J=8.1 Hz, 1H), 7.17-7.26 (m, 3H), 7.02-7.08 (m, 2H), 4.28 (q, J=7.2 Hz, 2H), 1.56 (t, J=7.2 Hz, 3H); ESI/MS: 436 (M+H).

(2-Chloro-5-trifluoromethylphenyl)-[2-(2,6-difluorophenoxy)-9-ethyl-9H-purin-8-yl]-amine: $^1$H NMR (300 MHz, CDCl$_3$) δ 9.12 (s, 1H), 8.55 (s, 1H), 7.58 (d, J=8.1 Hz, 1H), 7.18-7.34 (m, 3H), 7.03-7.09 (m, 2H), 4.28 (q, J=7.2 Hz, 2H), 1.56 (t, J=7.2 Hz, 3H); ESI/MS: 470 (M+H).

[2-(2,6-Difluorophenoxy)-9-ethyl-9H-purin-8-yl]-(2-methoxyphenyl)-amine: $^1$H NMR (300 MHz, CDCl$_3$) δ 8.54-8.57 (m, 1H), 8.46 (s, 1H), 7.18-7.24 (m, 2H), 6.96-7.12 (m, 4H), 4.24 (q, J=7.2 Hz, 2H), 4.00 (s, 3H), 1.53 (t, J=7.2 Hz, 3H); ES/MS: 398 (M+H).

{4-[8-(2-Chlorophenylamino)-9-ethyl-9H-purin-2-yloxy]-3,5-difluorophenyl}-carbamic acid tert-butyl ester: $^1$H NMR (300 MHz, CDCl$_3$) δ 8.66 (d, J=8.4 Hz, 1H), 8.50 (s, 1H), 7.39-7.48 (m, 2H), 7.05-7.16 (m, 3H), 6.63 (s, 1H), 4.26 (q, J=7.2 Hz, 2 H), 1.53-1.58 (m, 12H); ESI/MS: 517 (M+H).

[2-(4-Amino-2,6-difluorophenoxy)-9-ethyl-9H-purin-8-yl]-(2-chlorophenyl)-amine: $^1$H NMR (300 MHz, CDCl$_3$) δ 8.65 (d, J=8.1 Hz, 1H), 8.51 (s, 1H), 7.46 (dd, J=8.1, 1.5 Hz, 1H), 7.41 (dt, J=7.5, 1.5 Hz, 1H), 7.15 (br s, 1H), 7.07 (dt, J=7.8, 1.5 Hz, 1H), 6.34 (d, J=9.6 Hz, 2H), 4.27 (q, J=7.2 Hz, 2H), 1.56 (t, J=7.2 Hz, 3H); ESI/MS: 417 (M+H).

2-[2-(2,6-Difluorophenoxy)-9-ethyl-9H-purin-8-ylamino]-phenol: $^1$H NMR (300 MHz, CD$_3$OD) δ 8.23 (s, 1H), 7.68 (dd, J=8.1, 1.5 Hz, 1H), 7.27-7.35 (m, 1H), 7.08-7.17 (m, 3H), 6.94 (ddd, J=15.0, 7.8, 1.5 Hz, 2H), 4.22 (q, J=7.2 Hz, 2H), 1.43 (t, J=7.2 Hz, 3H); ESI/MS: 384 (M+H).

N-{4-[8-(2-Chlorophenylamino)-9-ethyl-9H-purin-2-yloxy]-3,5-difluorophenyl}-acetamide: $^1$H NMR (300 MHz, CD$_3$OD) δ 8.20 (s, 1H), 7.74 (br d, J=7.5 Hz, 1H), 7.56 (dd, J=8.1, 1.5 Hz, 1H), 7.39-7.46 (m, 3H), 7.30 (dt, J=7.8, 1.5 Hz, 1H), 4.25 (q, J=7.2 Hz, 2H), 2.18 (s, 3H), 1.45 (t, J=7.2 Hz, 3H); ESI/MS: 459 (M+H).

3-[2-(2,6-Difluorophenoxy)-9-ethyl-9H-purin-8-ylamino]-benzoic acid methyl ester: $^1$H NMR (300 MHz, CDCl$_3$) δ 8.48 (s, 1H), 8.14-8.19 (m, 2H), 7.82 (br d, J=7.5 Hz, 1H), 7.49-7.55 (m, 1H), 7.20-2.27 (m, 1H), 7.08 (t, J=7.5 Hz, 2H), 6.91 (bs, 1H), 4.27 (q, J=7.2 Hz, 2H), 3.98 (s, 3H), 1.53 (t, J=7.2 Hz, 3H); ESI/MS: 426 (M+H).

(2,6-Dichlorophenyl)-[2-(2,6-difluorophenoxy)-9-ethyl-9H-purin-8-yl]-amine: $^1$H NMR (300 MHz, CDCl$_3$) δ 8.19 (br s, 1H), 7.38 (br d, J=8.1 Hz, 2H), 7.16-7.23 (m, 1H), 7.04 (br t, J=7.8 Hz, 3H), 4.25 (q, J=7.2 Hz, 2H), 1.53 (t, J=7.2 Hz, 3H); ESI/MS: 436 (M+H).

Anal. calcd for C$_{19}$H$_{13}$Cl$_2$F$_2$N$_5$O (0.15H$_2$O): C, 51.99; H, 3.05; N, 15.95. Found: C, 52.01; H, 3.08; N, 15.48.

4-[8-(2-Chlorophenylamino)-9-ethyl-9H-purin-2-yloxy]-3,5-difluorobenzamide: $^1$H NMR (300 MHz, CDCl$_3$) δ 8.52 (s, 1H), 8.30 (unresolved dd, J=7.8 Hz, 1H), 7.49-7.55 (m, 2H), 7.42 (ddd app dt, J=7.8, 7.8, 1.8 Hz, 1H), 7.20 (ddd app dt, J=7.1, 7.1, 1.5 Hz, 1H), 6.15 (br s, 2H), 4.14 (q, J=7.2 Hz, 2H), 1.44 (t, J=7.2 Hz, 3H); $^{19}$F NMR (282 MHz, CD$_3$OD) δ 39.98 (d, J=7.6 Hz, 2 F); ESI/MS: 444.94 (M+H), HRMS (FAB) calc. for C$_{20}$H$_{16}$N$_6$O$_2$F$_2$Cl: 445.0991 found 445.0972 (M+H).

The compounds of the present invention which comprise Category III are 2-substituted-8-substituted-9-alkyl purines having the formula:

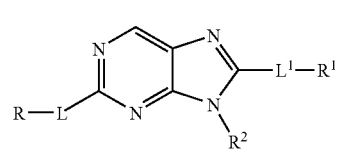

the first aspect of which relates to compounds having the formula:

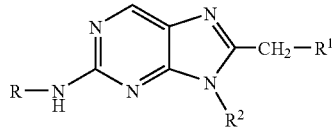

wherein non-limiting examples of R, $R^1$, and $R^2$ units are described herein below in Table V.

TABLE V

| No. | R | $R^1$ | $R^2$ |
|---|---|---|---|
| 127 | 2,6-difluorophenyl | 2-fluorophenyl | —$CH_2CH_3$ |
| 128 | 2,6-difluorophenyl | 4-fluorophenyl | —$CH_2CH_3$ |
| 129 | 2,6-difluorophenyl | 2-chlorophenyl | —$CH_2CH_3$ |
| 130 | 2,6-difluorophenyl | 2-fluoro-5-chlorophenyl | —$CH_2CH_3$ |
| 131 | 2,6-difluorophenyl | 2-chloro-5-fluorophenyl | —$CH_2CH_3$ |
| 132 | 2,6-difluorophenyl | 2,3-dichlorophenyl | —$CH_2CH_3$ |
| 133 | 2,6-difluorophenyl | 2-chloro-5-methylphenyl | —$CH_2CH_3$ |
| 134 | 2,6-difluorophenyl | 2-chloro-5-trifluoromethylphenyl | —$CH_2CH_3$ |
| 135 | 2,6-difluorophenyl | 2-aminophenyl | —$CH_2CH_3$ |
| 136 | 2,6-difluorophenyl | 2-nitrophenyl | —$CH_2CH_3$ |
| 137 | 2,6-difluorophenyl | 2-methoxyphenyl | —$CH_2CH_3$ |
| 138 | 2,6-difluorophenyl | 2-hydroxyphenyl | —$CH_2CH_3$ |
| 139 | 2,6-difluorophenyl | 3-methylcarboxyphenyl | —$CH_2CH_3$ |
| 140 | 2,6-difluorophenyl | 2,6-dichlorophenyl | —$CH_2CH_3$ |
| 141 | 2-fluorophenyl | 2-fluorophenyl | —$CH_2CH_3$ |
| 142 | 2-fluorophenyl | 4-fluorophenyl | —$CH_2CH_3$ |
| 143 | 2-fluorophenyl | 2-chlorophenyl | —$CH_2CH_3$ |
| 144 | 2-fluorophenyl | 2-fluoro-5-chlorophenyl | —$CH_2CH_3$ |
| 145 | 2-fluorophenyl | 2-chloro-5-fluorophenyl | —$CH_2CH_3$ |
| 146 | 2-fluorophenyl | 2,3-dichlorophenyl | —$CH_2CH_3$ |
| 147 | 2-fluorophenyl | 2-chloro-5-methylphenyl | —$CH_2CH_3$ |
| 148 | 2-fluorophenyl | 2-chloro-5-trifluoromethylphenyl | —$CH_2CH_3$ |
| 149 | 2-fluorophenyl | 2-aminophenyl | —$CH_2CH_3$ |
| 150 | 2-fluorophenyl | 2-nitrophenyl | —$CH_2CH_3$ |
| 151 | 2-fluorophenyl | 2-methoxyphenyl | —$CH_2CH_3$ |
| 152 | 2-fluorophenyl | 2-hydroxyphenyl | —$CH_2CH_3$ |
| 153 | 2-fluorophenyl | 3-methylcarboxyphenyl | —$CH_2CH_3$ |
| 154 | 2-fluorophenyl | 2,6-dichlorophenyl | —$CH_2CH_3$ |

The compounds which comprise the first aspect of Category III can be prepared by the procedure described herein below as outlined in Scheme II. Intermediate 8 can be prepared by the same procedure as outlined in Scheme II and described herein above.

Scheme IV

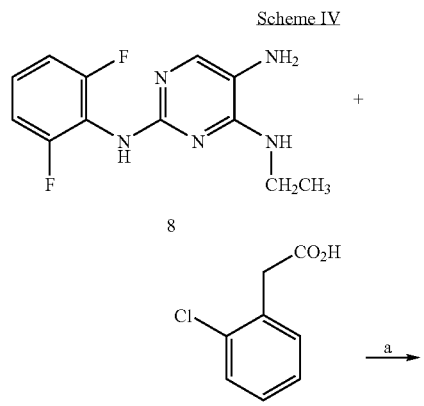

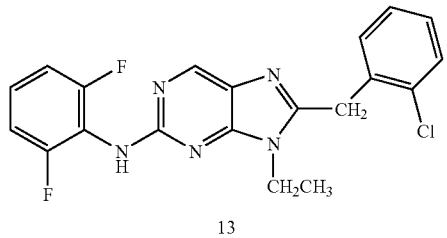

Reagents and conditions: (a) 150° C.; 18 hr.

EXAMPLE 4

Preparation of [8-(2-chlorobenzyl)-9-ethyl-9H-purin-2-yl]-(2,6-difluorophenyl)-amine (13): 2-Chlorophenyl acetic acid (0.27 g, 1.58 mmol) and N-2-(2,6-difluorophenyl)-N-4-ethyl-pyrimidine-2,4,5-triamine, 8, (0.21 g, 0.79 mmol) are combined and heated to 150° C. under $N_2$ for 18 hours. The mixture is diluted with saturated aqueous $NaHCO_3$ (100 mL) and extracted three times with EtOAc (200 mL). The combined organic layers are washed with water, dried over $MgSO_4$ and concentrated in vacuo to produce a residue which is purified over silica (20% EtOAc/hexane) to afford 83 mg (26% yield) of the desired product as a yellow solid. $^1$H NMR (300 MHz, $CDCl_3$) δ 8.72 (s, 1H), 7.44-7.47 (m, 1H), 7.15-7.27 (m, 4H), 6.98-7.03 (m, 3H), 4.38 (s, 2H), 4.05 (q, J=7.2 Hz, 2H), 1.25 (t, J=7.2 Hz, 3H); ESI/MS: 400 (M+H).

The second aspect of Category III relates to 2-oxy-purines having the formula:

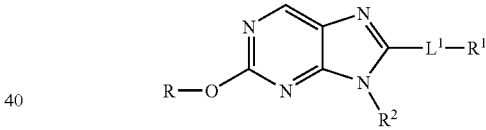

wherein $L^1$ units have the formula: —$NR^5$—; non-limiting examples of R, $R^1$, $R^2$, and $R^5$ are described in Table VI.

TABLE VI

| No. | R | $L^1$ | $R^1$ | $R^2$ |
|---|---|---|---|---|
| 155 | 2,6-difluorophenyl | —$CH_2CONHCH_3$ | 2-chlorophenyl | —$CH_3$ |
| 156 | 2,6-difluorophenyl | —$CH_2CON(CH_3)_2$ | 2-chlorophenyl | —$CH_3$ |
| 157 | 2,6-difluorophenyl | —$CH_2CO_2H$ | 2-chlorophenyl | —$CH_3$ |
| 158 | 2,6-difluorophenyl | —$CH_2CO_2CH_3$ | 2-chlorophenyl | —$CH_3$ |
| 159 | 2,6-difluorophenyl | —$CH_2CO_2C(CH_3)_3$ | 2-chlorophenyl | —$CH_3$ |
| 160 | 2,6-difluorophenyl | —$CH_2CH_2OH$ | 2-chlorophenyl | —$CH_3$ |
| 161 | 2,6-difluorophenyl | —$CH_2CONHCH_3$ | 2-chlorophenyl | —$CH_2CH_3$ |

TABLE VI-continued

| No. | R | L¹ | R¹ | R² |
|---|---|---|---|---|
| 162 | 2,6-difluorophenyl | —CH₂CON(CH₃)₂ | 2-chlorophenyl | —CH₂CH₃ |
| 163 | 2,6-difluorophenyl | —CH₂CO₂H | 2-chlorophenyl | —CH₂CH₃ |
| 164 | 2,6-difluorophenyl | —CH₂CO₂CH₃ | 2-chlorophenyl | —CH₂CH₃ |
| 165 | 2,6-difluorophenyl | —CH₂CO₂C(CH₃)₃ | 2-chlorophenyl | —CH₂CH₃ |
| 166 | 2,6-difluorophenyl | —CH₂CH₂OH | 2-chlorophenyl | —CH₂CH₃ |
| 167 | phenyl | —CH₂CONHCH₃ | 2-chlorophenyl | —CH₃ |
| 168 | phenyl | —CH₂CON(CH₃)₂ | 2-chlorophenyl | —CH₃ |
| 169 | phenyl | —CH₂CO₂H | 2-chlorophenyl | —CH₃ |
| 170 | phenyl | —CH₂CO₂CH₃ | 2-chlorophenyl | —CH₃ |
| 171 | phenyl | —CH₂CO₂C(CH₃)₃ | 2-chlorophenyl | —CH₃ |
| 172 | phenyl | —CH₂CH₂OH | 2-chlorophenyl | —CH₃ |
| 173 | phenyl | —CH₂CONHCH₃ | 2-chlorophenyl | —CH₂CH₃ |
| 174 | phenyl | —CH₂CON(CH₃)₂ | 2-chlorophenyl | —CH₂CH₃ |
| 175 | phenyl | —CH₂CO₂H | 2-chlorophenyl | —CH₂CH₃ |
| 176 | phenyl | —CH₂CO₂CH₃ | 2-chlorophenyl | —CH₂CH₃ |
| 177 | phenyl | —CH₂CO₂C(CH₃)₃ | 2-chlorophenyl | —CH₂CH₃ |
| 178 | phenyl | —CH₂CH₂OH | 2-chlorophenyl | —CH₂CH₃ |
| 179 | 2,6-difluorophenyl | —CH₂CONHCH₃ | 4-fluorophenyl | —CH₃ |
| 180 | 2,6-difluorophenyl | —CH₂CON(CH₃)₂ | 4-fluorophenyl | —CH₃ |
| 181 | 2,6-difluorophenyl | —CH₂CO₂H | 4-fluorophenyl | —CH₃ |
| 182 | 2,6-difluorophenyl | —CH₂CO₂CH₃ | 4-fluorophenyl | —CH₃ |
| 183 | 2,6-difluorophenyl | —CH₂CO₂C(CH₃)₃ | 4-fluorophenyl | —CH₃ |
| 184 | 2,6-difluorophenyl | —CH₂CH₂OH | 4-fluorophenyl | —CH₃ |
| 185 | 2,6-difluorophenyl | —CH₂CONHCH₃ | 4-fluorophenyl | —CH₂CH₃ |
| 186 | 2,6-difluorophenyl | —CH₂CON(CH₃)₂ | 4-fluorophenyl | —CH₂CH₃ |
| 187 | 2,6-difluorophenyl | —CH₂CO₂H | 4-fluorophenyl | —CH₂CH₃ |
| 188 | 2,6-difluorophenyl | —CH₂CO₂CH₃ | 4-fluorophenyl | —CH₂CH₃ |
| 189 | 2,6-difluorophenyl | —CH₂CO₂C(CH₃)₃ | 4-fluorophenyl | —CH₂CH₃ |
| 190 | 2,6-difluorophenyl | —CH₂CH₂OH | 4-fluorophenyl | —CH₂CH₃ |

The compounds which comprise the second aspect of Category III can be prepared by the procedure described herein below as outlined in Scheme V beginning with final analogs, for example, compound 14 which corresponds to analog 101 from Table IV.

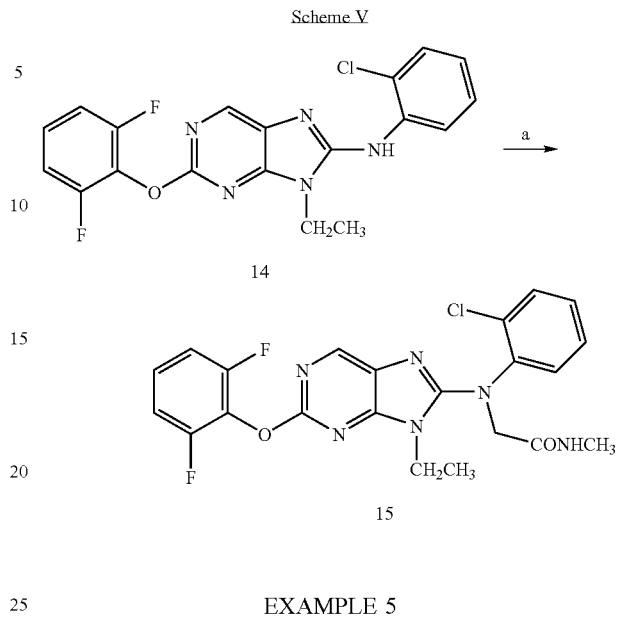

Scheme V

EXAMPLE 5

2-{(2-Chlorophenyl)-[2-(2,6-difluorophenoxy)-9-ethyl-9H-purin-8-yl]-amino}-N-methyl-acetamide: Sodium hydride (60% in oil, 0.010 g, 0.25 mmol) is added to a solution of [2-(2,6-difluorophenoxy)-9-ethyl-9H-purin-8-yl]-(2-chlorophenyl)-amine, 14, (0.1 g, 0.25 mmol) in THF (3 mL). After 5 minutes at room temperature 2-bromo-N-methyl-acetamide (0.06 mL, 0.37 mmol) is added and stirring is continued for 1 hour. The mixture is diluted with $H_2O$ (25 mL) and extracted three times with EtOAc (50 mL). The combined organic layers are washed with brine, dried over $MgSO_4$, concentrated in vacuo and the residue purified by HPLC to afford 45 mg (38% yield) of the desired product as a yellow solid. $^1H$ NMR (300 MHz, $CDCl_3$) δ 8.54 (s, 1H), 7.54-7.59 (m, 2H), 7.15-7.36 (m, 4H), 7.04 (t, J=7.8 Hz, 2H), 4.53 (s, 2H), 3.61 (q, J=7.2 Hz, 2H), 2.85 (d, J=4.8 Hz, 3H), 0.99 (t, J=7.2 Hz, 3H); ESI/MS: 473 (M+H).

The following are further non-limiting examples of the second aspect of Category III.

2-{(2-Chlorophenyl)-[2-(2,6-difluorophenoxy)-9-ethyl-9H-purin-8-yl]-amino}-N,N-dimethyl-acetamide: $^1H$ NMR (300 MHz, $CDCl_3$) δ 48.48 (s, 1H), 7.50-7.54 (m, 2 H), 7.28-7.35 (m, 2H), 7.15-7.21 (m, 1H), 7.02 (t, J=7.8 Hz, 2H), 4.76 (s, 2H), 3.62 (q, J=7.2 Hz, 2H), 3.09 (s, 3H), 3.01 (s, 3H), 1.10 (t, J=7.2 Hz, 3H); ESI/MS: 487 (M+H).

{(2-Chlorophenyl)-[2-(2,6-difluorophenoxy)-9-ethyl-9H-purin-8-yl]-amino}-acetic acid methyl ester: $^1H$ NMR (300 MHz, $CDCl_3$) δ 8.52 (s, 1H), 7.56 (dd, J=6.0, 3.3 Hz, 1H), 7.31-7.42 (m, 3H), 7.14-7.22 (m, 1H), 7.01-7.06 (m, 2H), 4.63 (s, 2H), 3.79 (s, 3H), 3.50 (q, J=7.2 Hz, 2H), 1.08 (t, J=7.2 Hz, 3H); ESI/MS: 474 (M+H).

{(2-Chlorophenyl)-[2-(2,6-difluorophenoxy)-9-ethyl-9H-purin-8-yl]-amino}-acetic acid: $^1H$ NMR (300 MHz, $CDCl_3$) δ 8.53 (s, 1H), 7.57-7.60 (m, 1H), 7.33-7.38 (m, 3H), 7.16-7.23 (m, 1H), 7.01-7.07 (m, 2H), 4.61 (s, 2H), 3.62 (q, J=7.2 Hz, 2H), 0.99 (t, J=7.2 Hz, 3H) ESI/MS: 460 (M+H).

{(2-Chlorophenyl)-[2-(2,6-difluorophenoxy)-9-ethyl-9H-purin-8-yl]-amino}-acetic acid tert-butyl ester: $^1H$ NMR (300 MHz, $CDCl_3$) δ 8.48 (s, 1H), 7.55 (dd, J=6.0, 3.6 Hz, 1H), 7.28-7.37 (m, 3H), 7.13-7.21 (m, 1H), 6.98-7.06 (m, 2H), 4.48 (s, 2 H), 3.59 (q, J=7.2 Hz, 2H), 1.47 (s, 9H), 1.05 (t, J=7.2 Hz, 3H); ESI/MS: 516 (M+H).

{(2-Chlorophenyl)-[2-(2,6-difluorophenoxy)-9-ethyl-9H-purin-8-yl]-amino}-ethanol: $^1$H NMR (300 MHz, CDCl$_3$) δ 8.50 (s, 1H), 7.59 (dd, J=6.0, 3.6 Hz, 1H), 7.32-7.38 (m, 2H), 7.16-7.29 (m, 2H), 7.01-7.08 (m, 2H), 4.12 (t, J=4.5 Hz, 2H), 3.83 (t, J=4.5 Hz, 2H), 3.63 (q, J=7.2 Hz, 2H), 0.96 (t, J=7.2 Hz, 3H); ESI/MS: 446 (M+H).

The third aspect of Category III relates to 2-substituted-8-[substituted or unsubstituted]-acyl-9-alkyl purines having the formula:

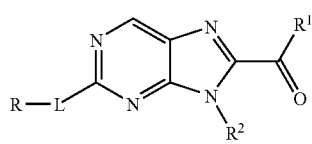

wherein non-limiting examples of L, R, R$^1$, and R$^2$ units are described herein below in Table VII.

TABLE VII

| No. | L | R | R$^1$ | R$^2$ |
|---|---|---|---|---|
| 191 | —NH— | 2-hydroxy-2-methyl-1-(S)-methylpropyl | 4-chlorophenyl | —CH$_3$ |
| 192 | —NH— | 2-hydroxy-2-methyl-1-(S)-methylpropyl | 4-chlorophenyl | —CH$_2$CH$_3$ |
| 193 | —NH— | 2-hydroxy-2-methyl-1-(S)-methylpropyl | 4-chlorophenyl | —CH(CH$_3$)$_2$ |
| 194 | —NH— | 2-hydroxy-2-methyl-1-(S)-methylpropyl | 2-chlorophenyl | —CH$_3$ |
| 195 | —NH— | 2-hydroxy-2-methyl-1-(S)-methylpropyl | 2-chlorophenyl | —CH$_2$CH$_3$ |
| 196 | —NH— | 2-hydroxy-2-methyl-1-(S)-methylpropyl | 2-chlorophenyl | —CH(CH$_3$)$_2$ |
| 197 | —NH— | 2-hydroxy-2-methyl-1-(S)-methylpropyl | 2-fluorophenyl | —CH$_3$ |
| 198 | —NH— | 2-hydroxy-2-methyl-1-(S)-methylpropyl | 2-fluorophenyl | —CH$_2$CH$_3$ |
| 199 | —NH— | 2-hydroxy-2-methyl-1-(S)-methylpropyl | 2-fluorophenyl | —CH(CH$_3$)$_2$ |
| 200 | —NH— | 2-methoxy-1-(S)-methylethyl | 4-chlorophenyl | —CH$_3$ |
| 201 | —NH— | 2-methoxy-1-(S)-methylethyl | 4-chlorophenyl | —CH$_2$CH$_3$ |
| 202 | —NH— | 2-methoxy-1-(S)-methylethyl | 4-chlorophenyl | —CH(CH$_3$)$_2$ |
| 203 | —NH— | 2-methoxy-1-(S)-methylethyl | 2-chlorophenyl | —CH$_3$ |
| 204 | —NH— | 2-methoxy-1-(S)-methylethyl | 2-chlorophenyl | —CH$_2$CH$_3$ |
| 205 | —NH— | 2-methoxy-1-(S)-methylethyl | 2-chlorophenyl | —CH(CH$_3$)$_2$ |
| 206 | —NH— | 2-methoxy-1-(S)-methylethyl | 2-fluorophenyl | —CH$_3$ |
| 207 | —NH— | 2-methoxy-1-(S)-methylethyl | 2-fluorophenyl | —CH$_2$CH$_3$ |
| 208 | —NH— | 2-methoxy-1-(S)-methylethyl | 2-fluorophenyl | —CH(CH$_3$)$_2$ |
| 209 | —O— | 2,6-difluorophenyl | 4-chlorophenyl | —CH$_3$ |
| 210 | —O— | 2,6-difluorophenyl | 4-chlorophenyl | —CH$_2$CH$_3$ |
| 211 | —O— | 2,6-difluorophenyl | 4-chlorophenyl | —CH(CH$_3$)$_2$ |
| 212 | —O— | 2,6-difluorophenyl | 2-chlorophenyl | —CH$_3$ |
| 213 | —O— | 2,6-difluorophenyl | 2-chlorophenyl | —CH$_2$CH$_3$ |
| 214 | —O— | 2,6-difluorophenyl | 2-chlorophenyl | —CH(CH$_3$)$_2$ |
| 215 | —O— | 2,6-difluorophenyl | 2-fluorophenyl | —CH$_3$ |
| 216 | —O— | 2,6-difluorophenyl | 2-fluorophenyl | —CH$_2$CH$_3$ |
| 217 | —O— | 2,6-difluorophenyl | 2-fluorophenyl | —CH(CH$_3$)$_2$ |
| 218 | —O— | pyran-4-yl | 4-chlorophenyl | —CH$_3$ |
| 219 | —O— | pyran-4-yl | 4-chlorophenyl | —CH$_2$CH$_3$ |
| 220 | —O— | pyran-4-yl | 4-chlorophenyl | —CH(CH$_3$)$_2$ |
| 221 | —O— | pyran-4-yl | 2-chlorophenyl | —CH$_3$ |

TABLE VII-continued

| No. | L | R | R$^1$ | R$^2$ |
|---|---|---|---|---|
| 222 | —O— | pyran-4-yl | 2-chlorophenyl | —CH$_2$CH$_3$ |
| 223 | —O— | pyran-4-yl | 2-chlorophenyl | —CH(CH$_3$)$_2$ |
| 224 | —O— | pyran-4-yl | 2-fluorophenyl | —CH$_3$ |
| 225 | —O— | pyran-4-yl | 2-fluorophenyl | —CH$_2$CH$_3$ |
| 226 | —O— | pyran-4-yl | 2-fluorophenyl | —CH(CH$_3$)$_2$ |
| 227 | —O— | piperidin-4-yl | 4-chlorophenyl | —CH$_3$ |
| 228 | —O— | piperidin-4-yl | 4-chlorophenyl | —CH$_2$CH$_3$ |
| 229 | —O— | piperidin-4-yl | 4-chlorophenyl | —CH(CH$_3$)$_2$ |
| 230 | —O— | piperidin-4-yl | 2-chlorophenyl | —CH$_3$ |
| 231 | —O— | piperidin-4-yl | 2-chlorophenyl | —CH$_2$CH$_3$ |
| 232 | —O— | piperidin-4-yl | 2-chlorophenyl | —CH(CH$_3$)$_2$ |
| 233 | —O— | piperidin-4-yl | 2-fluorophenyl | —CH$_3$ |
| 234 | —O— | piperidin-4-yl | 2-fluorophenyl | —CH$_2$CH$_3$ |
| 235 | —O— | piperidin-4-yl | 2-fluorophenyl | —CH(CH$_3$)$_2$ |

The compounds which comprise the third aspect of Category III can be prepared by the procedure described herein below as outlined in Scheme VI beginning with intermediate 6.

Scheme VI

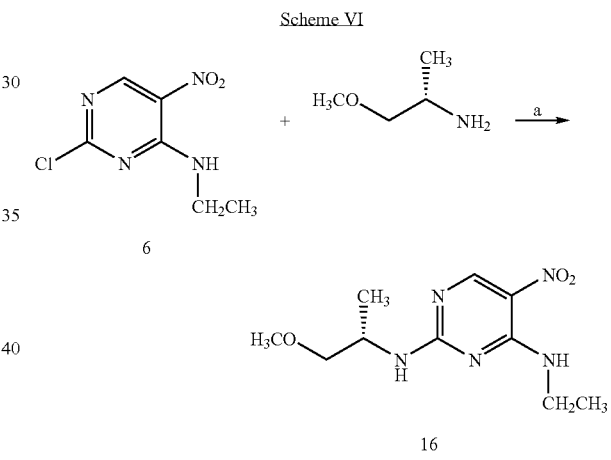

Reagents and conditions: (a) Na; rt, 1 hr.

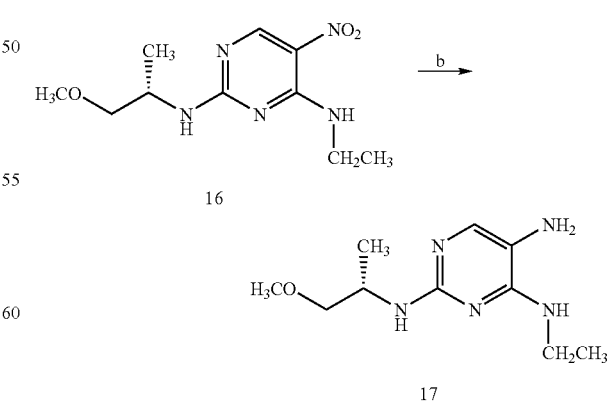

Reagents and conditions: (b) H$_2$, Pd/C, EtOH; 40° C., 1.5 hr.

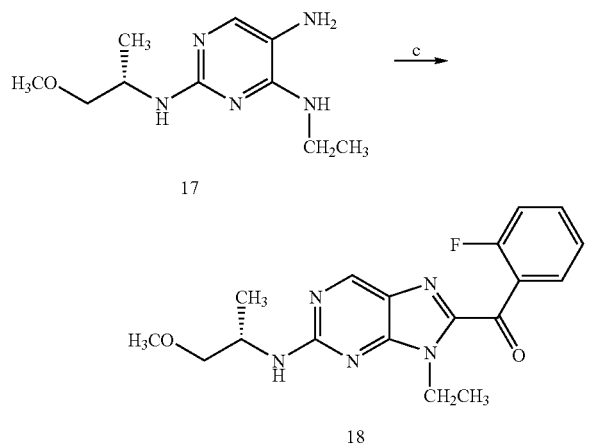

Reagents and conditions: (c) i) 2-fluoro-benzimidic acid ethyl ester, EtOH; reflux, 18 hr; ii) MnO$_2$, CH$_2$Cl$_2$; rt, 1 hr.

EXAMPLE 6

[9-Ethyl-2-(S)-(2-methoxy-1-methyl-ethoxy)-9H-purin-8-yl]-(2-fluoro-phenyl)-methanone (18)

Preparation of ethyl-[2-(S)-(2-methoxy-1-methyl-ethoxy)-5-nitro-pyrimidin-4-yl]-amine (16): Sodium metal (0.08 g, 3.57 mmol) is added to (S)-(+)-1-methoxy-2-propanol (0.35 mL, 3.57 mmol) and the mixture stirred at room temperature under N$_2$ until homogenous after which (2-chloro-5-nitro-pyrimidin-4-yl)-ethyl-amine, 6, (0.5 g, 2.5 mmol) is added and the mixture stirred for 1 hour. The reaction is then diluted with H$_2$O (20 mL), extracted three times with EtOAc (50 mL), washed with brine, the combined organic layers dried over MgSO$_4$ and then concentrated in vacuo. The resulting residue is purified over silica (40% EtOAc/hexanes) to afford 0.14 g (22% yield) of the desired product as a yellow solid. $^1$H NMR (300 MHz, CDCl$_3$) δ 9.01 (s, 1 H), 8.41 (br s, 1H), 5.38-5.44 (m, 1H), 3.67 (q, J=7.2 Hz, 2H), 3.64 (d, J=4.2 Hz, 1 H), 3.54 (d, J=4.2 Hz, 1H), 3.40 (s, 3H), 1.39 (d, J=6.6 Hz, 3H), 1.33 (t, J=7.2 Hz, 3 H); ESI/MS: 185 (M–C$_4$H$_8$).

Preparation of N-4-ethyl-2-(S)-(2-methoxy-1-methyl-ethoxy)-pyrimidine-4,5-diamine (17): To a solution of ethyl-[2-(S)-(2-methoxy-1-methyl-ethoxy)-5-nitro-pyrimidin-4-yl]-amine, 16, (0.14 g, 0.55 mmol) in EtOH (4 mL) is added palladium on carbon (0.02 g). The mixture is stirred under an atmosphere of hydrogen gas at 40° C. for 1.5 hours. The reaction is cooled, filtered through Celite® to remove the catalyst and the filtrate concentrated to afford 0.1 g (80% yield) of the desired product as a yellow solid. ESI/MS: 227 (M+H).

Preparation of [9-ethyl-2-(S)-(2-methoxy-1-methyl-ethoxy)-9H-purin-8-yl]-(2-fluoro-phenyl)-methanone (18): To a solution of N-4-ethyl-2-(S)-(2-methoxy-1-methyl-ethoxy)-pyrimidine-4,5-diamine, 17, (0.075 g, 0.33 mmol) in EtOH (3 mL) is added 2-fluoro-benzimidic acid ethyl ester HCl salt (0.075 g, 0.37 mmol), which can be prepared by the procedure of Guerret et al., *J. Heterocyclic Chem.*, 1983, 20, 1525 included herein by reference. The mixture is heated to reflux for 18 hours, cooled and concentrated in vacuo. The crude alcohol thus obtained (0.1 g, 0.28 mmol) is treated with manganese oxide (0.12 g, 1.39 mmol) in CH$_2$Cl$_2$ (3 mL). After 1 hour at room temperature the mixture is filtered through Celite® and concentrated in vacuo to a residue which is purified over silica (30% EtOAc/hexane) to afford 0.014 g (12% yield) of the desired product as a yellow solid. $^1$H NMR (300 MHz, CDCl$_3$) δ 9.05 (s, 1H), 7.84 (td, J=7.2 Hz, 1.8 Hz, 1H), 7.59-7.67 (m, 1H), 7.34 (td, J=7.5 Hz, 0.9 Hz, 1H), 7.20-7.26 (m, 1H), 5.53-5.59 (m, 1H), 4.71 (q, J=7.2 Hz, 2H), 3.75 (dd, J=10.2 Hz, 6.6 Hz, 1H), 3.60 (dd, J=10.2 Hz, 4.2 Hz, 1H), 3.45 (s, 3H), 1.55 (t, J=7.2 Hz, 3H), 1.47 (d, J=6.6 Hz, 3H); ESI/MS: 359 (M+H). HRMS (FAB) calc. for C$_{18}$H$_{19}$FN$_4$O$_3$: 359.1519 found 359.1508 (M+H).

The following are non-limiting examples of compounds which comprise the third aspect of Category III.

(4-Chlorophenyl)-[2-(2-hydroxy-1,2-dimethyl-propylamino)-9-methyl-9H-purin-8-yl]-methanone: $^1$H NMR (300 MHz, CDCl$_3$) δ 8.87 (s, 1H), 8.33 (d, J=9.0 Hz, 2H), 7.53 (d, J=9.0 Hz, 2H), 5.60 (br d, J=7.2 Hz, 1H), 4.19-4.24 (m, 1H), 4.07 (s, 3H), 1.31-1.36 (m, 9H); ESI/MS: 374 (M+H).

(2-Chlorophenyl)-[2-(2,6-difluorophenoxy)-9-ethyl-9H-purin-8-yl]-methanone:
$^1$H NMR (300 MHz, CDCl$_3$) δ 9.02 (s, 1H), 7.48-7.72 (m, 4H), 7.32-7.42 (m, 1H), 7.15-7.21 (m, 2H), 4.64 (q, J=6.9 Hz, 2H), 1.49 (t, J=7.5 Hz, 3H); $^{19}$F NMR (282 MHz, CDCl$_3$) δ 34.00 (m, 2 F); (FAB) calc. for C$_{20}$H$_{14}$N$_4$F$_2$O$_2$Cl: 415.0773 found 415.0762 (M+H).

8-(2-chlorobenzenesulfonyl)-2-(2,6-difluorophenoxy)-9-ethyl-9H-purine: $^1$H NMR (300 MHz, CDCl$_3$) δ 8.93 (s, 1H), 7.58-7.64 (m, 2H), 7.43-7.50 (m, 2H), 7.20-7.26 (m, 1H), 7.06 (t, J=7.8 Hz, 2H), 4.59 (q, J=7.2 Hz, 2H), 1.53 (t, J=7.2 Hz, 3 H); ESI/MS: 435 (M+H). HRMS (FAB) calc. for C$_{19}$H$_{13}$ClF$_2$N$_4$O$_2$S: 435.0494 found 435.0506 (M+H).

[2-(2,6-Difluorophenoxy)-9-ethyl-9H-purin-8-yl]-(2-fluorophenyl)-methanone: $^1$H NMR (300 MHz, CDCl$_3$) δ 9.04 (s, 1H), 7.82-7.88 (m, 1H), 7.60-7.68 (m, 1H), 7.20-7.37 (m, 3H), 7.07 (t, J=7.5 Hz, 2H), 4.67 (q, J=6.9 Hz, 2H), 1.53 (t, J=7.2 Hz, 3H); $^{19}$F NMR (282 MHz, CDCl$_3$) δ 52.46 (m, 1 F), 37.00 (m, 2 F); (FAB) calc. for C$_{20}$H$_{14}$N$_4$F$_3$O$_2$: 399.1069 found 399.1065 (M+H).

[9-Ethyl-2-(R)-(2-methoxy-1-methyl-ethoxy)-9H-purin-8-yl]-(2-fluorophenyl)-methanone: $^1$H NMR (300 MHz, CDCl$_3$) δ 9.05 (s, 1H), 7.85 (td, J=7.5 Hz, 1.8 Hz, 1H), 7.60-7.67 (m, 1H), 7.34 (td, J=7.5 Hz, 0.9 Hz, 1H), 7.20-7.27 (m, 1H), 5.53-5.59 (m, 1H), 4.71 (q, J=7.2 Hz, 2H), 3.75 (dd, J=10.2 Hz, 6.6 Hz, 1H), 3.60 (dd, J=10.2 Hz, 4.2 Hz, 1H), 3.45 (s, 3H), 1.55 (t, J=7.2 Hz, 3H), 1.47 (d, J=6.6 Hz, 3H). HRMS (FAB) calc. for C$_{18}$H$_{19}$FN$_4$O$_3$: 359.1519 found 359.1524 (M+H).

[9-Ethyl-2-(2-methoxy-ethoxy)-9H-purin-8-yl]-(2-fluorophenyl)-methanone: $^1$H NMR (300 MHz, CDCl$_3$) δ 9.05 (s, 1H), 7.84 (td, J=7.2 Hz, 1.8 Hz, 1H), 7.59-7.67 (m, 1H), 7.34 (td, J=7.5 Hz, 0.9 Hz, 1H), 7.20-7.26 (m, 1H), 4.71 (q, J=7.2 Hz, 2H), 4.67 (t, J=4.8 Hz, 2H), 3.86 (t, J=4.8 Hz, 2H), 3.48 (s, 3H), 1.54 (t, J=7.2 Hz, 3H). HRMS (FAB) calc. for C$_{17}$H$_{17}$FN$_4$O$_3$: 345.1363 found 345.1355 (M+H).

(2-Chlorophenyl)-[2-(2,6-difluorophenoxy)-9-isopropyl-9H-purin-8-yl]-methanone:
ESI/MS: 431 (M+H). $^1$H NMR (300 MHz, CDCl$_3$) δ 9.03 (s, 1H), 7.64-7.69 (m, 1H), 7.44-7.55 (m, 3H), 7.20-7.26 (m, 1H), 7.08 (t, J=8.1 Hz, 2H), 5.48 (sep, J=7.2 Hz, 1H), 1.69 (d, J=7.2 Hz, 6H); ESI/MS: 429 (M+H).

(2-Chlorophenyl)-[9-isopropyl-2-(tetrahydro-pyran-4-yloxy)-9H-purin-8-yl]-methanone: $^1$H NMR (300 MHz, CDCl$_3$) δ 8.86 (s, 1H), 7.48 (dd, J=8.1, 1.8 Hz, 1H), 7.32-7.42 (m, 3H), 6.47 (s, 1H), 5.23 (sep, J=4.2 Hz, 1H), 4.50 (quin, J=6.9 Hz, 1H), 4.03-4.10 (m, 2H), 2.13-2.20 (m, 2H), 1.90-2.01 (m, 2H), 1.67 (d, J=6.9 Hz, 3H), 1.34 (d, J=6.9 Hz, 3H); ESI/MS: 403 (M+H). ¹H NMR (300 MHz, CDCl₃) δ 9.01 (s, 1H), 7.68 (dd, J=7.5 Hz, 2.1 Hz, 1H), 7.44-7.56 (m, 3H), 5.57 (quin, J=6.9 Hz, 1H), 5.31 (sep, J=4.2 Hz, 1H), 4.06-4.13 (m, 2H), 3.65-3.73 (m, 2H), 2.16-2.23 (m, 2H), 1.94-2.05 (m, 2H), 1.81 (d, J=6.9 Hz, 6H); ESI/MS: 401 (M+H).

The compounds of the present invention which comprise Category IV are 2-[substituted or unsubstituted aryl]-oxy-8-substituted-9-alkyl purines having the formula:

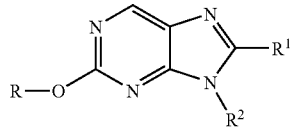

wherein non-limiting examples of R, R¹, and R² are defined herein below in Table VIII

TABLE VIII

| No. | R | R¹ | R² |
|---|---|---|---|
| 236 | 2,6-difluorophenyl | 2-fluorophenyl | —CH₂CH₃ |
| 237 | 2,6-difluorophenyl | 4-fluorophenyl | —CH₂CH₃ |
| 238 | 2,6-difluorophenyl | 2-chlorophenyl | —CH₂CH₃ |
| 239 | 2,6-difluorophenyl | 2-fluoro-5-chlorophenyl | —CH₂CH₃ |
| 240 | 2,6-difluorophenyl | 2-chloro-5-fluorophenyl | —CH₂CH₃ |
| 241 | 2,6-difluorophenyl | 2,3-dichlorophenyl | —CH₂CH₃ |
| 242 | 2,6-difluorophenyl | 2-chloro-5-methylphenyl | —CH₂CH₃ |
| 243 | 2,6-difluorophenyl | 2-chloro-5-trifluoromethylphenyl | —CH₂CH₃ |
| 244 | 2,6-difluorophenyl | 2-aminophenyl | —CH₂CH₃ |
| 245 | 2,6-difluorophenyl | 2-nitrophenyl | —CH₂CH₃ |
| 246 | 2,6-difluorophenyl | 2-methoxyphenyl | —CH₂CH₃ |
| 247 | 2,6-difluorophenyl | 2-hydroxyphenyl | —CH₂CH₃ |
| 248 | 2,6-difluorophenyl | 3-methylcarboxyphenyl | —CH₂CH₃ |
| 249 | 2,6-difluorophenyl | 2,6-dichlorophenyl | —CH₂CH₃ |
| 250 | 2-fluorophenyl | 2-fluorophenyl | —CH₂CH₃ |
| 251 | 2-fluorophenyl | 4-fluorophenyl | —CH₂CH₃ |
| 252 | 2-fluorophenyl | 2-chlorophenyl | —CH₂CH₃ |
| 253 | 2-fluorophenyl | 2-fluoro-5-chlorophenyl | —CH₂CH₃ |
| 254 | 2-fluorophenyl | 2-chloro-5-fluorophenyl | —CH₂CH₃ |
| 255 | 2-fluorophenyl | 2,3-dichlorophenyl | —CH₂CH₃ |
| 256 | 2-fluorophenyl | 2-chloro-5-methylphenyl | —CH₂CH₃ |
| 257 | 2-fluorophenyl | 2-chloro-5-trifluoromethylphenyl | —CH₂CH₃ |
| 258 | 2-fluorophenyl | 2-aminophenyl | —CH₂CH₃ |
| 259 | 2-fluorophenyl | 2-nitrophenyl | —CH₂CH₃ |
| 260 | 2-fluorophenyl | 2-methoxyphenyl | —CH₂CH₃ |
| 261 | 2-fluorophenyl | 2-hydroxyphenyl | —CH₂CH₃ |
| 262 | 2-fluorophenyl | 3-methylcarboxyphenyl | —CH₂CH₃ |
| 263 | 2-fluorophenyl | 2,6-dichlorophenyl | —CH₂CH₃ |

The compounds which comprise the first aspect of Category IV can be prepared by the procedure described herein below and outlined in Scheme VII.

Scheme VII

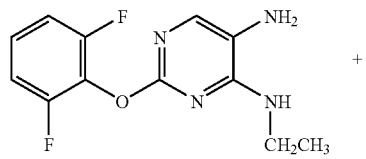

11

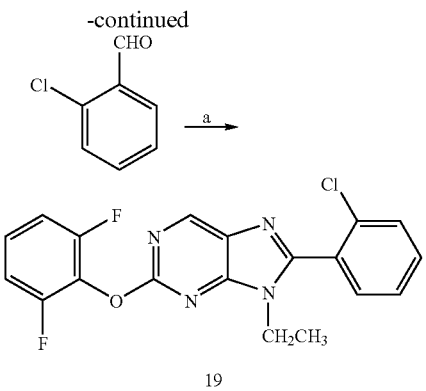

Reagents and conditions: (a) FeCl₃/SiO₂; dioxane; 110° C., 18 hr.

EXAMPLE 7

Preparation of 8-(2-chlorophenyl)-2-(2,6-difluorophenoxy)-9-ethyl-9H-purine (19): To a stirred solution of 2-(2,6-difluorophenoxy)-N-4-ethyl-pyrimidine-4,5-diamine, 11, (0.1 g, 0.38 mmol) in dioxane (10 mL) is added 2-chlorobenzaldehyde (0.05 mL, 0.45 mmol) and FeCl₃.SiO₂ (0.17 g, 0.75 mmol). The mixture is heated to 110° C. for 18 hours. After cooling the mixture is filtered and concentrated in vacuo. The crude residue is purified by preparative HPLC to afford 23 mg (16% yield) of the desired product as a red solid. ¹H NMR (300 MHz, CDCl₃) δ 8.90 (s, 1H), 7.45-7.62 (m, 4H), 7.19-7.26 (m, 1H), 7.07 (t, J=7.8 Hz, 2H), 4.14 (q, J=7.2 Hz, 2H), 1.31 (t, J=7.2 Hz, 3H); ESI/MS: 387 (M+H). Anal. calcd for C₁₉H₁₃ClF₂N₄O (0.5H₂O): C, 57.66; H, 3.57; N, 14.16. Found: C, 57.61; H, 2.83; N, 14.46.

The following are non-limiting examples of the first aspect of Category IV.

4-[8-(2-Chlorophenylamino)-9-ethyl-9H-purin-2-yloxy]-3,5-difluorobenzoic acid methyl ester: ¹H NMR (300 MHz, CDCl₃) δ 8.62 (br d, J=7.8 Hz, 1H), 8.48 (br s, 1H), 7.75 (m, 2H), 7.47 (d, J=8.4 Hz, 1H), 7.42 (t, J=8.1 Hz, 1H), 7.10 (dt, J=7.2 Hz, 1H), 4.26 (q, J=7.2 Hz, 2H), 3.97 (s, 3H), 1.55 (t, J=7.8 Hz, 3H); ¹⁹F NMR (282 MHz, CDCl₃) δ 38.83 (d, J=6.2 Hz, 2 F); HRMS (FAB) calc. for C₂₁H₁₆N₅O₃F₂Cl: 460.0987 found 460.0972 (M+H).

4-[8-(2-Chlorophenylamino)-9-ethyl-9H-purin-2-yloxy]-3,5-difluorobenzoic acid: ¹H NMR (300 MHz, CD₃OD) δ 8.25 (s, 1H), 7.74-7.81, 7.72(m overlapping dd, J=7.8, 1.5 Hz, 3H), 7.62 (dd, J=8.1, 1.5 Hz, 1H), 7.47 (dt, J=15.3, 2.1 Hz, 1H), 7.38 (dt, J=15.0, 1.8 Hz, 1H), 4.29 (q, J=7.2 Hz, 2H), 1.47 (t, J=7.5 Hz, 3H); ¹⁹F NMR (282 MHz, CD₃OD) δ 35.78 (d, J=6.2 Hz, 2 F); HRMS (FAB) calc. for C₂₀H₁₄N₅O₃F₂C₁-446.0831 found 446.0842 (M+H).

8-(2-Chloro-phenyl)-2-(2,6-difluoro-phenoxy)-9-ethyl-9H-purine: ¹H NMR (300 MHz, CDCl₃) δ 8.90 (s, 1H), 7.45-7.62 (m, 4H), 7.19-7.26 (m, 1H), 7.07 (t, J=7.8 Hz, 2H), 4.14 (q, J=7.2 Hz, 2H), 1.31 (t, J=7.2 Hz, 3H); ESI/MS: 387 (M+H). Anal. calcd for C₁₉H₁₃ClF₂N₄O (0.5H₂O): C, 57.66; H, 3.57; N, 14.16. Found: C, 57.61; H, 2.83; N, 14.46.

The following are non-limiting examples of other compounds according to the present invention.

3-[8-(2-Chlorophenyl)-9-methyl-9H-purin-2-ylamino]-2-methyl-butan-2-ol: ¹H NMR (300 MHz, CDCl₃) δ 8.71 (s, 1H), 7.52-7.59 (m, 3H), 7.46 (dq, J=7.2, 1.8 Hz, 1H), 5.34 (d, J=8.1 Hz, 1H), 4.15 (quin, J=7.2 Hz, 1H), 3.58 (s, 3H), 1.34 (s, 3H), 1.31 (d, J=6.9 Hz, 3H), 1.28 (s, 3H); ESI/MS: 346 (M+H). Anal. calcd for $C_{17}H_{20}ClN_5O(0.1H_2O)$: C, 58.74; H, 5.86; N, 20.15. Found: 58.70; H, 5.13; N, 19.83.

N-8-(2-Chlorophenyl)-N-2-(2,6-difluoro-phenyl)-9-ethyl-9H-purine-2,8-diamine: $^1$H NMR (300 MHz, $CDCl_3$) δ 8.63 (d, J=8.1 Hz, 1H), 8.51 (s, 1H), 7.36-7.45 (m, 1H), 7.12-7.22 (m, 1H), 6.98-7.06 (m, 4H), 6.91 (br s, 1H), 4.14 (q, J=7.2 Hz, 2H), 1.49 (t, J=7.2 Hz, 3H). ESI/MS: 401 (M+H).

[8-(2-Chlorobenzyl)-9-ethyl-9H-purin-2-yl]-(2,6-difluorophenyl)-amine: $^1$H NMR (300 MHz, $CDCl_3$) δ 8.72 (s, 1H), 7.44-7.47 (m, 1H), 7.15-7.27 (m, 4H), 6.98-7.03 (m, 3H), 4.38 (s, 2H), 4.05 (q, J=7.2 Hz, 2H), 1.25 (t, J=7.2 Hz, 3H); ESI/MS: 400 (M+H).

3-[8-(2-Chlorobenzylamino)-9-methyl-9H-purin-2-ylamino]-2-methyl-butan-2-ol: $^1$H NMR (300 MHz, $CDCl_3$) δ 8.21 (s, 1H), 7.53 (dd, J=5.7, 3.6 Hz, 1H), 7.40-7.43 (m, 1H), 7.26-7.31 (m, 2H), 4.94 (d, J=7.5 Hz, 1H), 4.81 (s, 2H), 4.01 (quin, J=7.2 Hz, 1H), 3.47 (s, 3H), 1.30 (s, 3H), 1.25 (d, J=6.9 Hz, 3H), 1.23 (s, 3H). ESI/MS: 375 (M+H).

N-8-(2-Chlorophenyl)-9-(4-fluoro-phenyl)-N-2-(tetrahydro-pyran-4-yl)-9H-purine-2,8-diamine: $^1$H NMR (300 MHz, $CDCl_3$) δ 8.73 (dd, J=8.1, 0.9 Hz, 1H), 8.50 (s, 1H), 7.53-7.58 (m, 2H), 7.34-7.40 (m, 4H), 7.09 (br s, 1H), 7.00 (dd, J=7.8, 1.5 Hz, 1H), 4.92 (br d, J=7.8 Hz, 1H), 4.02, 3.98 (m overlapping ddd (app dt's), J=11.7, 11.7, 2.7 Hz, 3H), 3.54 (ddd (app dt's), J=11.4, 11.4, 1.8 Hz, 2H), 2.03-2.06 (m, 2H). $^{19}$F NMR ($CDCl_3$) δ 53.07 (s, 1 F), HRMS (FAB) calc. for $C_{22}H_{21}N_6OFCl$: 439.1449 found 439.1427 (M+H).

2-Chloro-N-[9-methyl-2-(tetrahydro-pyran-4-ylamino)-9H-purin-8-yl]-benzenesulfonamide: $^1$H NMR (300 MHz, $CDCl_3$) δ 8.14 (s, 1H), 7.51-7.65 (m, 4H), 7.32 (br s, 1H), 7.12 (br s, 1H), 5.06 (d, J=6.3 Hz, 1H), 3.95-4.04 (m, 3H), 3.53 (dt, J=11.4, 2.1 Hz, 2H), 3.30 (s, 3H), 2.00-2.04 (m, 2H), 1.47-1.60 (m, 2H); ESI/MS: 423 (M+H).

2-Chloro-N-[9-methyl-2-(tetrahydro-pyran-4-ylamino)-9H-purin-8-yl]-benzamide: $^1$H NMR (300 MHz, $CDCl_3$) δ 8.19 (s, 1H), 8.00-8.03 (m, 1H), 7.46-7.49 (m, 1H), 7.34-7.40 (m, 2H), 5.10 (d, J=7.8 Hz, 1H), 7.02-4.12 (m, 3H), 3.65 (s, 3H), 3.60 (dt, J=11.4, 2.1 Hz, 2H), 2.10 (br d, J=12.6 Hz, 2H), 1.54-1.67 (m, 2H); ESI/MS: 387 (M+H).

3-[9-(4-Fluorophenyl)-8-(4-fluorophenylamino)-9H-purin-2-ylamino]-(S)-2-methyl-butan-2-ol: $^1$H NMR (300 MHz, $CDCl_3$) δ 8.38 (s, 1H), 7.49-7.60 (m, 4H), 7.37 (t app, J=8.1 Hz, 2H), 7.07 (t app, J=8.4 Hz, 2H), 6.17 (br s, 1H), 4.98 (br d, J=7.5 Hz, 1H), 3.94-4.03 (m, 1H), 1.27 (s, 3H), 1.19 (s, 3H); $^{19}$F NMR ($CDCl_3$) δ 53.36 (s, 1 F), 43.66 (t, J=3.3 Hz, 1 F); HRMS (FAB) calc. for $C_{22}H_{23}N_6OF_2$: 425.1901 found 425.1899 (M+H).

3-[2-(2,6-Difluorophenoxy)-9-ethyl-9H-purin-8-ylamino]-benzoic acid methyl ester: $^1$H NMR (300 MHz, $CDCl_3$) δ 8.48 (s, 1H), 8.14-8.19 (m, 2H), 7.82 (br d, J=7.5 Hz, 1H), 7.49-7.55 (m, 1H), 7.20-2.27 (m, 1H), 7.08 (t, J=7.5 Hz, 2H), 6.91 (bs, 1H), 4.27 (q, J=7.2 Hz, 2H), 3.98 (s, 3H), 1.53 (t, J=7.2 Hz, 3H); ESI/MS: 426 (M+H).

3-[8-[2-(2-Chlorophenyl)-ethylamino]-9-methyl-9H-purin-2-ylamino]-2-(S)-methyl-butan-2-ol: $^1$H NMR (300 MHz, $CDCl_3$) δ 8.19 (s, 1H), 7.38-7.42 (m, 1H), 7.21-7.26 (m, 3H), 5.11 (br s, 1H), 4.41 (t, J=5.7 Hz, 1H), 4.03 (quin, J=7.2 Hz, 1H), 3.83 (q, J=6.3 Hz, 2H), 3.39 (s, 1H), 3.19 (t, J=6.6 Hz, 2H). ESI/MS: 389 (M+H).

3-{8-[(4-Chlorophenyl)-hydroxy-methyl]-9-methyl-9H-purin-2-ylamino}-2-methyl-butan-2-ol: $^1$H NMR (300 MHz, $CDCl_3$) δ 8.52 (s, 1H), 7.31-7.38 (m, 4H), 6.01 (s, 1H), 5.31 (d, J=8.1 Hz, 1H), 4.06-4.13 (m, 1H), 3.42 (s, 3H), 1.24-1.30 (m, 9H); ESI/MS: 376 (M+H).

2-Chloro-N-[9-(4-fluorophenyl)-2-(tetrahydro-pyran-4-ylamino)-9H-purin-8-yl]-benzamide: $^1$H NMR (300 MHz, $CDCl_3$) δ 8.61 (d, J=6.9 Hz, 1H), 8.28 (s, 1H), 7.78 (d, J=7.2 Hz, 1H), 7.66-7.70 (m, 2H), 7.20-7.38 (m, 5H), 6.76 (d, J=6.6 Hz, 1H), 5.01 (br d, J=11.1 Hz, 1H), 4.79 (br unresolved t, 1H), 3.99 (bd, J=11.1 Hz, 3H), 3.53 (t, J=11.7 Hz, 2H), 2.04 (bd, J=11.1 Hz, 2H), 1.47-1.60 (m, 2H); $^{19}$F NMR ($CDCl_3$) δ 50.40 (s, 1 F), HRMS (FAB) calc. for $C_{23}H_{21}N_6O_2FCl$: 467.1398 found 467.1378 (M+H).

9-(4-Fluorophenyl)-N-2-(tetrahydro-pyran-4-yl)-9H-purine-2,8-diamine: $^1$H NMR (300 MHz, $CDCl_3$) δ 8.31 (s, 1H), 7.47-7.51 (m, 2H), 7.29-7.35 (m, 2H), 4.96 (br d, 1H), 4.73 (br s, 2H), 3.95-4.07 (m overlapping ddd (app dt), J=11.4, 6.9, 3.9 Hz, 3 H), 3.53 (ddd (app dt's), J=11.7, 11.7 2.4 Hz, 2H), 2.02-2.06 (m, 2H), 1.45-1.59 (m, 2H); $^{19}$F NMR ($CDCl_3$) δ 52.30 (s, 1 F), HRMS (FAB) calc. for $C_{16}H_{18}N_6OF$: 329.1526 found 329.1527 (M+H).

2-Chloro-N-[9-(4-fluorophenyl)-2-(tetrahydro-pyran-4-ylamino)-9H-purin-8-yl]-benzenesulfonamide: $^1$H NMR (300 MHz, $CDCl_3$) δ 8.61 (d, J=7.5 Hz, 1H), 7.19-7.67 (m, 8H), 3.93-3.98 (m, 2H), 3.48 (t, J=11.4 Hz, 2H), 1.97 (br d, J=12.3 Hz, 2 H), 1.43-1.56 (m, 2H); HRMS (FAB) calc. for $C_{22}H_{21}N_6O_3FSCl$: 503.1068 found 503.1081 (M+H).

6-(2-Chlorophenyl)-3-fluoro-10-(tetrahydro-pyran-4-ylamino)-6H-6,7,9,11,11b-pentaaza-benzo[c]fluoren-5-one: $^1$H NMR (300 MHz, $CDCl_3$) δ 8.38 (dd, J=9.3, 4.5 Hz, 1H), 8.59(br s, 1H), 8.12 (dd, J=7.8, 3.0 Hz, 1H), 7.28-7.71 (m, 5H), 4.12-4.25 (m, 1H), 4.09 (ddd (app dt), J=11.4, 3.6 Hz, 2H), 3.65 (t app, J=11.1, Hz, 2 H), 3.08-3.16 (m, 1H), 2.17 (br d, J=13.2, Hz 2H), 1.48 (s, 3H), 1.46 (s, 3H); HRMS (FAB) calc. for $C_{23}H_{19}N_6O_2FCl$: 465.1242 found 465.1254 (M+H).

[8-(2-Chlorophenylamino)-2-(2-hydroxy-1,2-dimethyl-propylamino)-purin-9-yl]-acetic acid methyl ester: $^1$H NMR (300 MHz, $CDCl_3$) δ 9.43 (br s, 1H), 8.31 (br d, J=7.8 Hz, 1H), 8.03 (s, 1H), 7.69 (d, J=8.1 Hz, 1H), 7.40 (t, J=7.5 Hz, 1H), 7.29 (s, 1H), 7.13 (t, J=8.1 Hz, 1H), 4.94 (s, 2H), 4.18 (m, 1H), 3.97 (s, 3H), 3.72-3.79 (m, 1 H), 1.25-1.34 (m, 10H); HRMS (FAB) calc. for $C_{19}H_{23}N_6O_3Cl$: 419.1598 found 419.1605 (M+H).

[8-(2-Chlorophenylamino)-2-(2-hydroxy-1,2-dimethyl-propylamino)-purin-9-yl]-acetic acid: $^1$H NMR (300 MHz, $CD_3OD$) δ 8.16 (br s, 1H), 8.01 (dd, J=8.4, 1.2 Hz, 1H), 7.44 (dd, J=8.1, 1.5 Hz, 1H), 7.32 (dt, J=8.1, 1.5 Hz, 1H), 7.05 (dt, J=8.1, 1.5 Hz, 1H), 4.71 (br s, 2H), 4.13 (m, 1H), 1.17-1.31 (overlapping d's, 9H); HRMS (FAB) calc. for $C_{18}H_{22}N_6O_3Cl$: 405.1441 found 405.1430 (M+H).

3-[8-(2-Chlorophenylamino)-9-(2-hydroxy-ethyl)-9H-purin-2-ylamino]-(S)-2-methyl-butan-2-ol: $^1$H NMR (300 MHz, $CD_3OD$) δ 8.18 (br s, 1H), 8.12 (br d, J=7.8 Hz, 1H), 7.45 (dd, J=8.1, 1.5 Hz, 1H), 7.33 (ddd, J=8.1, 7.2, 1.5 Hz, 1H), 7.05 (ddd, J=8.1, 7.2 1.5 Hz, 1H), 4.26 (t, J=4.2 Hz, 1H), 4.07-4.14 (m, 1H), 3.96 (t, J=4.5 Hz, 1H), 1.23-1.27 (overlapping d's, 9H); HRMS (FAB) calc. for $C_{18}H_{24}N_6O_2Cl$: 391.1649 found 391.1638 (M+H).

2-{(2-Chlorophenyl)-[2-(2,6-difluorophenoxy)-9-ethyl-9H-purin-8-yl]-amino}-N-methyl-acetamide: $^1$H NMR (300 MHz, $CDCl_3$) δ 8.54 (s, 1H), 7.54-7.59 (m, 2H), 7.15-7.36 (m, 4H), 7.04 (t, J=7.8 Hz, 2H), 4.53 (s, 2H), 3.61 (q, J=7.2 Hz, 2H), 2.85 (d, J=4.8 Hz, 3H), 0.99 (t, J=7.2 Hz, 3H); ESI/MS: 473 (M+H).

2-{(2-Chlorophenyl)-[2-(2,6-difluorophenoxy)-9-ethyl-9H-purin-8-yl]-amino}-N,N-dimethyl-acetamide: $^1$H NMR (300 MHz, $CDCl_3$) δ 48.48 (s, 1H), 7.50-7.54 (m, 2 H), 7.28-7.35 (m, 2H), 7.15-7.21 (m, 1H), 7.02 (t, J=7.8 Hz, 2H), 4.76 (s, 2H), 3.62 (q, J=7.2 Hz, 2H), 3.09 (s, 3H), 3.01 (s, 3H), 1.10 (t, J=7.2 Hz, 3H); ES/MS: 487 (M+H).

2-{(2-Chlorophenyl)-[2-(2,6-difluorophenoxy)-9-ethyl-9H-purin-8-yl]-amino}-ethanol: $^1$H NMR (300 MHz, CDCl$_3$) δ 8.50 (s, 1H), 7.59 (dd, J=6.0, 3.6 Hz, 1H), 7.32-7.38 (m, 2H), 7.16-7.29 (m, 2-H), 7.01-7.08 (m, 2H), 4.12 (t, J=4.5 Hz, 2H), 3.83 (t, J=4.5 Hz, 2H), 3.63 (q, J=7.2 Hz, 2H), 0.96 (t, J=7.2 Hz, 3H); ES/MS: 446 (M+H).

{(2-Chlorophenyl)-[2-(2,6-difluorophenoxy)-9-ethyl-9H-purin-8-yl]-amino}-acetic acid tert-butyl ester: $^1$H NMR (300 MHz, CDCl$_3$) δ 8.48 (s, 1H), 7.55 (dd, J=6.0, 3.6 Hz, 1H), 7.28-7.37 (m, 3H), 7.13-7.21 (m, 1H), 6.98-7.06 (m, 2H), 4.48 (s, 2 H), 3.59 (q, J=7.2 Hz, 2H), 1.47 (s, 9H), 1.05 (t, J=7.2 Hz, 3H); ESI/MS: 516 (M+H).

{(2-Chlorophenyl)-[2-(2,6-difluorophenoxy)-9-ethyl-9H-purin-8-yl]-amino}-acetic acid: $^1$H NMR (300 MHz, CDCl$_3$) δ 8.53 (s, 1H), 7.57-7.60 (m, 1H), 7.33-7.38 (m, 3H), 7.16-7.23 (m, 1H), 7.01-7.07 (m, 2H), 4.61 (s, 2H), 3.62 (q, J=7.2 Hz, 2H), 0.99 (t, J=7.2 Hz, 3H) ESI/MS: 460 (M+H).

{(2-Chlorophenyl)-[2-(2,6-difluorophenoxy)-9-ethyl-9H-purin-8-yl]-amino}-acetic acid methyl ester: $^1$H NMR (300 MHz, CDCl$_3$) δ 8.52 (s, 1H), 7.56 (dd, J=6.0, 3.3 Hz, 1H), 7.31-7.42 (m, 3H), 7.14-7.22 (m, 1H), 7.01-7.06 (m, 2H), 4.63 (s, 2H), 3.79 (s, 3H), 3.50 (q, J=7.2 Hz, 2H), 1.08 (t, J=7.2 Hz, 3H); ESI/MS: 474 (M+H).

Compounds listed and described herein above have been found in many instances to exhibit activities (IC$_{50}$ in the cell based assay described herein below or ones which are referenced herein) at a level below 1 micromolar (μM).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines.

Inflammatory Disease States

Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease states which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBS), septic shock, cardiopulmonary dysfunction, acute respiratory disease, and cachexia.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Formulations

The present invention also relates to compositions or formulations which comprise the inflammatory cytokine release-inhibiting compounds according to the present invention. In general, the compositions of the present invention comprise:

a) an effective amount of one or more 2,8,9-substituted purines and derivatives thereof according to the present invention which are effective for inhibiting release of inflammatory cytokines; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of compositions according to the present invention include:

a) from about 0.001 mg to about 1000 mg of one or more 2,8,9-substituted purines according to the present invention; and b) one or more excipient.

Another embodiment according to the present invention relates to the following compositions:

a) from about 0.01 mg to about 100 mg of one or more 2,8,9-substituted purines according to the present invention; and b) one or more pharmaceutical excipient.

A further embodiment according to the present invention relates to the following compositions:

a) from about 0.1 mg to about 10 mg of one or more 2,8,9-substituted purines according to the present invention; and b) one or more pharmaceutical excipient.

The term "effective amount" as used herein means "an amount of one or more 2,8,9-substituted purines, effective at dosages and for periods of time necessary to achieve the desired result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

Method of Use

The present invention also relates to a method for controlling the level of one or more inflammation inducing cytokines, inter alia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

The present invention also relates to the use of the 2,8,9-substituted purines according to the present invention in the manufacture of a medicament for the treatment of inflammatory cytokine related disorders. These disorders are described herein above under Inflammatory Disease States.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

Procedures

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:
i) UV-visible substrate enzyme assay as described by L. Al Reiter, *Int. J. Peptide Protein Res.*, 43, 87-96 (1994).
ii) Fluorescent substrate enzyme assay as described by Thornberry et al., *Nature*, 356, 768-774 (1992).
iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:
i) K. M. Mohler et al., "Protection Against a Lethal Dose of Endotoxin by an Inhibitor of Tumour Necrosis Factor Processing", *Nature*, 370, pp 218-220 (1994).
ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells ($2\times10^6$ cells/mL, final conc.; American Type Culture Company, Rockville, Md.) are added to 96 well polypropylene round bottomed culture plates (Costar 3790; sterile) containing 125 µL test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 µg/mL final; Sigma L-2630, from *E. coli* serotype 0111.B4; stored as 1 mg/mL stock in endotoxin screened diluted $H_2O$ vehicle at –80° C.). Blanks (unstimulated) receive $H_2O$ vehicle; final incubation volume is 250 µL. Incubation (4 hours) proceeds as described above. Assay is to be terminated by centrifuging plates 5 minutes at room temperature, 1600 rpm (4033 g); supernatants are then transferred to clean 96 well plates and stored at –80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A compound chosen from:
   N-8-(2-Chlorophenyl)-9-methyl-N-2-(tetrahydro-pyran-4-yl)-9H-purine-2,8-diamine;
   N-8-(2-Fluorophenyl)-9-methyl-N-2-(tetrahydro-pyran-4-yl)-9H-purine-2,8-diamine;
   N-8-(2-Chlorophenyl)-N-2-(2,6-difluorophenyl)-9-ethyl-9H-purine-2,8-diamine;
   N-8-(2-Chlorophenyl)-N-2-(4-fluorophenyl)-9-methyl-9-H-purine-2,8-diamine;
   N-8-(2-Chlorophenyl)-N-2-(2,4-difluorophenyl)-9-methyl-9H-purine-2,8-diamine;
   N-8-(2-Chlorophenyl)-N-2-(2,4-difluorophenyl)-9-methyl-9H-purine-2,8-diamine;
   N-8-(2-Chlorophenyl)-N-2(2,6-difluorophenyl)-9-isopropyl-9H-purine-2,8-diamine;
   N-8-(2-Chlorophenyl)-2-(2,6-difluorophenyl)-9H-purine-2,8-diamine;
   3-[8-(2-Chlorophenylamino)-2-(2,6-difluorophenamino)-purin-9-yl]-(S)-2-methyl-butan-2-ol;
   9-Butyl-N-8-(2-chlorophenyl)-N-2-(2,6-difluorophenyl)-9H-purine-2,8-diamine;
   N-8-(2-Chlorophenyl)-9-cyclopropyl-N-2-(2,6-difluorophenyl)-9H-purine-2,8-diamine;
   9-tert-Butyl-N-8(2-chlorophenyl)-N-2-(2,6-difluorophenyl)-9H-purine-2,8-diamine;
   N-8-(2-Chloro-4-fluorophenyl)-N-2-(2,6-difluorophenyl)-9-ethyl-9H-purine-2,8-diamine;
   N-8-(2-Chlorophenyl)-N-2-(2,6-difluorophenyl)-9-methyl-9H-purine-2,8-diamine;
   3-[8-(2-Chlorophenylamino)-9-methyl-9H-purin-2-ylamino]-2-methyl-butan-2-ol;
   [2-(2,6-Difluorophenoxy)-9-ethyl-9H-purin-8-yl]-(fluorophenyl)-amine;
   [2-(2,6-Difluoro-phenoxy)-9-ethyl-9H-purin-8-yl]-o-tolyl-amine;
   (2-Chloro-phenyl)-[2-(2,6-difluoro-phenoxy)-9-ethyl-9H-purin-8-yl]-amine;
   (2-Chlorophenyl)-[2-(2,6-difluoro-4-methylaminomethyl-phenoxy)-9-ethyl-9H-purin-8-yl]-amine;

[2-(2,6-Difluorophenoxy)-9-ethyl-9H-8-yl]-(2-nitrophenyl)-amine;
N-[2-(2,6-Difluorophenoxy)-9-ethyl-9H-purin-8-yl]-benzene-1,2-diamine;
4-[8-(2-Chlorophenylamino)-9-ethyl-9H-purin-2-yloxy]-3,5-difluoro-N-methyl-benzamide;
(2-Chlorophenyl)-[9-ethyl-2-(2-fluoro-phenoxy-9H-purin-8-yl]-amine;
(2-Chloro-5-fluorophenyl)-[2-(2,6-difluorophenoxy)-9-ethyl-9H-purin-8-yl]-amine;
(2-Chloro-5-methylphenyl)-[2-(2,6-difluorophenoxy)-9-ethyl-9H-purin-8-yl]-amine;
(2,3-Dichlorophenyl)-[2-(2,6-difluorophenoxy)-9-ethyl-9H-purin-8-yl]-amine;
(2-Chloro-5-trifluoromethylphenyl)-[2-(2,6-difluorophenoxy)-9-ethyl-9H-purin-8-yl]-amine;
[2-(2,6-Difluorophenoxy)-9-ethyl-9H-purin-8-yl]-(2-methoxyphenyl)-amine;
{4-[2-Chlorophenylamino)-9-ethyl-9H-purin-2-yloxy]-3,5-difluorophenyl}-carbamic acid tert-butyl ester;
[2-(4-Amino-2,6-difluorophenoxy)-9-ethyl-9H-purin-8-yl]-(2-chlorophenyl)-amine;
2-[2-(2,6-Difluorophenoxy)-9-ethyl-9H-purin-8-ylamino]-phenol;
N-{4-[8-(2-Chlorophenylamino)-9-ethyl-9H-purin-2-yloxy]-3,5-difluorophenyl}-acetamide;
3-[2-(2,6-Difluorophenoxy)-9-ethyl-9H-purin-8-ylamino]-benzoic acid methyl ester;
(2,6-Dichlorophenyl)-[2-(2-6-difluorophenoxy)-9-ethyl-9H-purin-8-yl]-amine; and
4-[8-(2-Chlorophenylamino)-9-ethyl-9H-purin-2-yloxy]-3,5-difluorobenzamide.

2. A compound chosen from:
[8-(2-Chlorobenzyl)-9-ethyl-9H-purin-2-yl]-2,6-difluorophenyl)-amine;
2-{(2-Chlorophenyl)-[2-(2,6-difluorophenoxy)-9-ethyl-9H-purin-8-yl]-amino}-N-methyl-acetamide;
2-{(2-Chlorophenyl)-[2-(2,6-difluorophenoxy)-9-ethyl-9H-purin-8-yl]-amino}-N,N-dimethyl-acetamide;
{(2-Chlorophenyl)-[2-(2,6-difluorophenoxy)-9-ethyl-9H-purin-8-yl]-amino}-acetic acid methyl ester;
{(2-Chlorophenyl)-[2-(2,6-difluorophenoxy)-9-ethyl-9H-purin-8-yl]-amino}-acetic acid;
{(2-Chlorophenyl)-[2-(2,6-difluorophenoxy)-9-ethyl-9H-purin-8-yl]-amino}-acetic acid tert-butyl ester;
2-{(2-Chlorophenyl)-[2-(2,6-difluorophenoxy)-9-ethyl-9H-purin-8-yl]-amino}-ethanol;
[9-Ethyl-2-(S)-(2-methoxy-1-methyl-ethoxy)-9H-purin-8-yl]-(2-fluoro-phenyl)-methanone;
(4-Chlorophenyl)-[2-(2-hydroxy-1,2-dimethyl-propylamino)-9-methyl-9H-purin-8-yl]-methanone;
(2-Chlorophenyl)-[2-(2,6-difluorophenoxy)-9-ethyl-9H-purin-8-yl]-methanone;
8-(2-chlorobenzenesulfonyl)-2-(2,6-difluorophenoxy)-9-ethyl-9H-purine;
[2-(2,6-Difluorophenoxy)-9-ethyl-9H-purin-8-yl]-(2-fluorophenyl)-methanone;
[9-Ethyl-2-(R)-(2-methoxy-1-methyl-ethoxy)-9H-purin-8-yl]-(2-fluorophenyl)-methanone;
[9-Ethyl-2-(2-methoxy-ethoxy)-9H-purin-8-yl]-(2-fluorophenyl)-methanone;
(2-Chlorophenyl)-[2-(2,6-difluorophenoxy)-9-isopropyl-9H-purin-8-yl]-methanone;
(2-Chlorophenyl)-[9-isopropyl-2-(tetrahydro-pyran-4-yloxy)-9H-purin-8-yl]-methanone;
8-(2-Chlorophenyl)-2-(2,6-difluorophenoxy)-9-ethyl-9H-purine;
4-[8-(2-Chlorophenylamino)-9-ethyl-9H-purin-2-yloxy]-3,5-difluorobenzoic acid methyl ester;
4-[8-(2-Chlorophenylamino)-9-ethyl-9H-purin-2-yloxy]-3,5-difluorobenzoic acid; and
8-(2-Chloro-phenyl)-2-(2,6-difluoro-phenoxy)-9-ethyl-9H-purine.

3. A compound chosen from:
3-[8(2-Chlorophenyl)-9-methyl-9H-purin-2-ylamino]-2-methyl-butan-2-ol;
N-8-(2-Chlorophenyl)-N-2-(2,6-difluoro-phenyl)-9-ethyl-9H-purine-2,8-diamine;
[8-(2-Chlorobenzyl)-9-ethyl-9H-purin-2-yl]-(2,6-difluorophenyl)-amine;
3-[8-(2-Chlorobenzylamino)-9-methyl-9H-purin-2-yl]-2-methyl-butan-2-ol;
N-8-(2-Chlorophenyl)-9-(4-fluoro-phenyl)-N-2-(tetrahydro-pyran-4-yl)-9H-purine-2,8-diamine;
2-Chloro-N-[9-methyl-2-(tetrahydro-pyran-4-ylamino)-9H-purin-8-yl]-benzenesulfonamide;
2-Chloro-N-[9-methyl-2-(tetrahydro-pyran-4-ylamino)-9H-purin-8-yl]-benzamide;
3-[9-(4-Fluorophenyl)-8-(4-fluorophenylamino)-9H-purin-ylamino]-(S)-2-methyl-butan-2-ol;
3-[2-(2,6-Difluorophenoxy)-9-ethyl-9H-purin-8-ylamino]-benzoic acid methyl ester;
3-{8-[2-(2-chlorophenyl)-ethylamino]-9-methyl-9H-purin-2-ylamino}-2-(S)-methyl-butan-2-ol;
3-{8 [(4-Chlorophenyl)-hydroxy-methyl]-9-methyl-9H-purin-2-ylamino}-2-methyl-butan-2-ol;
2-Chloro-N-[9-(4-fluorophenyl)-2-(tetrahydro-pyran-4-ylamino)-9H-purin-8-yl]-benzamide;
9-(4-Fluorophenyl)-N-2-(tetrahydro-pyran-4-yl)-9H-purine-2,8-diamine;
2-Chloro-N-[9-(4-fluorophenyl)-2-(tetrahydro-pyran-4-ylamino)-9H-purin-8-yl]-benzenesulfonamide;
6-(2-Chlorophenyl)-3-fluoro-10-(tetrahydro-pyran-4-ylamino)-6H-6,7,8,9,11,11b-pentaaza-benzo [c]fluoren-5-one;
[8-(2-Chlorophenylamino)-2-(2-hydroxy-1,2-dimethyl-propylamino)-purin-9-yl]-acetic acid methyl ester;
[8-(2-Chlorophenylamino)-2-(2-hydroxy-1,2-dimethyl-propylamino)-purin-9-yl]-acetic acid;
3-[8(2-Chlorophenylamino)-9-(2-hydroxy-ethyl)-9H-purin-2-ylamino]-(S)-2-methyl-butan-2-ol;
2-{(2-Chlorophenyl)-[2-(2,6-difluorophenoxy)-9-ethyl-9H-purin-8-yl]-amino}-N-methyl-acetamide;
2-{(2-Chlorophenyl)-[2-(2,6-difluorophenoxy)-9-ethyl-9H-purin-8-yl]-amino}-N,N-dimethyl-acetamide;
2-{(2-Chlorophenyl)-[2-(2,6-difluorophenoxy)-9-ethyl-9H-purin-8-yl]-amino}-ethanol;
{(2-Chlorophenyl)-[2-(2,6-difluorophenoxy)-9-ethyl-9H-purin-8-yl]-amino}-acetic acid tert-butyl ester;
{(2-Chlorophenyl)-[2-(2,6-difluorophenoxy)-9-ethyl-pu-rin-8-yl]-amino}-acetic acid; and
{(2-Chlorophenyl)-[2-(2,6-difluorophenoxy)-9-ethyl-9H-purin-yl]-amino}-acetic acid methyl ester.

4. A composition comprising:
a) an effective amount of one or more compounds according to claim 1; and
b) one or more pharmaceutically acceptable excipients.

5. A composition comprising:
a) an effective amount of one or more compounds according to claim 2; and
b) one or more pharmaceutically acceptable excipients.

6. A composition comprising:
a) an effective amount of one or more compounds according to claim 3; and
b) one or more pharmaceutically acceptable excipients.

* * * * *